United States Patent [19]

Tempesta et al.

[11] Patent Number: 5,681,829

[45] Date of Patent: Oct. 28, 1997

[54] CLASS OF PHOSPHOCHOLINE DERIVATIVES HAVING ANTIFUNGAL ACTIVITY

[75] Inventors: Michael Tempesta, Moss Beach; Shivanand D. Jolad, San Carlos; Steven King, Moss Beach; Guohua Mao; Reimar C. Bruening, both of San Carlos; John E. Kuo, Mountain View; Thien V. Troung, Emeryville; Donald E. Bierer; Jeffrey M. Dener, both of Daly City, all of Calif.

[73] Assignee: Shaman Pharmaceuticals, Inc., South San Francisco, Calif.

[21] Appl. No.: 411,709

[22] PCT Filed: Oct. 8, 1993

[86] PCT No.: PCT/US93/09623

§ 371 Date: Apr. 5, 1995

§ 102(e) Date: Apr. 5, 1995

[87] PCT Pub. No.: WO94/08563

PCT Pub. Date: Apr. 28, 1994

Related U.S. Application Data

[63] Continuation-in-part of Ser. No. 958,416, Oct. 8, 1992, abandoned.

[51] Int. Cl.$^6$ .............................. A61K 31/66; C07F 9/02
[52] U.S. Cl. .............................. 514/78; 514/76; 514/114; 558/166; 558/169
[58] Field of Search .................. 424/195.1; 514/25, 514/76, 78, 114; 536/4.1, 17.2, 17.9; 546/1, 292; 548/700; 549/5, 13, 29; 558/70, 88, 156, 166, 169

[56] References Cited

U.S. PATENT DOCUMENTS

| | | | |
|---|---|---|---|
| 4,408,052 | 10/1983 | Hozumi et al. | 546/22 |
| 4,595,681 | 6/1986 | Snyder et al. | 514/77 |
| 4,684,625 | 8/1987 | Eppstein et al. | 514/19 |
| 4,725,588 | 2/1988 | Snyder et al. | 514/114 |
| 5,087,721 | 2/1992 | Counsell et al. | 558/166 |

FOREIGN PATENT DOCUMENTS

| | | |
|---|---|---|
| 0 050 460 | 10/1981 | European Pat. Off. . |
| 0 138 559 | 10/1984 | European Pat. Off. . |
| 0 534 445 | 9/1992 | European Pat. Off. . |
| 38 29 899 | 9/1988 | Germany . |
| 58035194 | 3/1983 | Japan . |
| 58170792 | 10/1983 | Japan . |
| WO 94/08563 | 4/1994 | WIPO . |

OTHER PUBLICATIONS

Tetrahedron Letters, vol. 37, 1979, Van Boeckel et al pp. 3561–3564.

De Boer et al., 1976, "The Structure of Teichoic Acid from *Bacillus subrilis* var. *niger* WM as Determined by $^{13}$C Nuclear–Magnetic–Resonance Spectroscopy", Eur. J. Biochem. 62:1–6.

Ogawa et al., 1979, "Synthesis of the Repeating Unit of the Teichoic Acid Isolated from the Cell Wall of *Bacillus subtilis* VAR. *niger* WM", Carbohydrate Research 70:37–46.

Tsushima et al., 1982, "Syntheses and Antimicrobial Activities of Alkyl Lysophospholipids", Chem. Pharm. Bull. 30:3260–3270.

van Boeckel et al., 1983, "Synthesis of a Teichoic Acid Fragment of *Bacillus subtilis* Using a Modified Phosphotriester approach", Recl. Trav. Chim. Pays–Bas 102:526–537.

*Primary Examiner*—Elli Peselev
*Attorney, Agent, or Firm*—Pennie & Edmonds

[57] ABSTRACT

Certain phosphocholine derivatives having substantial antifungal therapeutic activity are disclosed. The phosphocholine derivatives may be chemically synthesized, enzymatically prepared or extracted from the plant *Irlbachia alata*. The phosphocholine derivatives are useful in treating fungal infections including those which are dermatophytic, systemic, ophthalmic and vaginal.

16 Claims, 3 Drawing Sheets

5,681,829

CLASS OF PHOSPHOCHOLINE DERIVATIVES HAVING ANTIFUNGAL ACTIVITY

This is a continuation-in-part application of U.S. patent application Ser. No. 07/958,416, filed Oct. 8, 1992, now abandoned, the entire disclosure of which is incorporated by reference.

1. FIELD OF THE INVENTION

This invention relates to new classes of phosphocholine derivatives as well as to various methods for preparing these compounds—including synthetic, enzymatic and extractive using certain plants. The phosphocholine derivatives of the invention are non-toxic and exhibit substantial antifungal activity in slowing fungal growth and in killing fungi.

2. BACKGROUND OF THE INVENTION

The plant species *Irlbachia alata* has been used as an anti-infective agent in the Peruvian Amazon region. The leaves are squeezed and the liquid is applied to infected skin sores. The same liquid from the leaves is applied to skin problems and skin fungal infections. It is utilized to treat vaginal yeast infections.

*Irlbachia alata* is one species of 10–12 species of the plant family Gentianaceae. These species occur in tropical South America especially in the Amazon and Negro River basins. The plants in the genus Irlbachia are generally low herbs characteristically with 3–5 plinerved leaves. The most consistent diagnostic feature for the genus is the pollen morphology.

A reference to *Irlbachia alata* and related species was made in 1775 by the French scientist Fusee Aublet (Aublet, F. 1775, Histoire des Plantes de la Guiane Francoise, Didot, Paris). The ethnobotanical notes from this reference were subsequently compiled and republished in English. Aublet noted the following about two species in the genus Irlbachia:

*Irlbachia Alata* The entire plant is bitter. It is used to clear obstructions; I (Aublet) have used it with good results. The species is called "Bois creux" (Hollow wood) by the Creoles.

*Irlbachia Pururascens* All parts of this plant are bitter. It is used as an apertif and to reduce fever.

3. SUMMARY OF THE INVENTION

We have discovered a class of phosphocholine derivatives (Class I) having extraordinary antifungal activity.

Structurally, these compounds are phosphocholine derivatives (1 or 2-deacyl-phosphatidyl cholines) in which the 1 or 2-OH-group of the glycerol moiety has been glycosylated with glucose, galactose, arabinose, mannose, rhamnose or another sugar. The basic chemical structure may be drawn as follows:

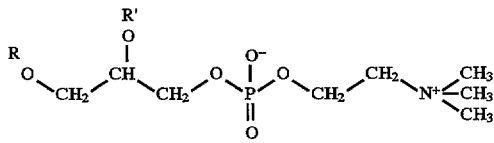

wherein one of R or R' is a sugar moiety and the other is an acyl or sugar moiety.

The molecular backbone common to all members of this class of compounds is drawn above. The acyl-group can be any long-chain fatty acid, while the sugar unit can be any of the sugars commonly found in plants, including but not limited to glucose, galactose, arabinose, mannose, rhamnose, or another naturally occurring sugar.

We have additionally found a structurally related class of phosphocholine derivatives of similar or greater antifungal activity than the above-discussed class of phosphocholine derivatives (i.e., Class I).

One novel class of phosphocholine derivatives (Class II) having antifungal activity has the basic structure shown below:

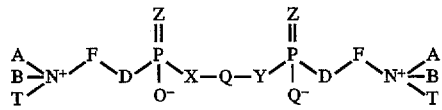

where Q is C2 to C30 alkyl, alkenyl, alkynyl, branched alkyl, branched alkenyl, or branched alkynyl;

Z is oxygen or sulfur; X and Y are independent oxygen, sulfur, $CH_2$, $CF_2$, or $N-R_1$;

A, B, and T are independently alkyl, alkenyl, alkynyl, branched alkyl, branched alkenyl, or branched alkynyl radicals of C1 to C20 chain lengths; are independently or together cycloalkyl or bridged cycloalkyl radicals of ring size C3 to C20, or cylcoalkenyl, bridged cycloalkenyl or cyclo(polyene)radicals of ring size C4 to C20, cycloalkynyl, bridged cycloalkeynl or cyclo (polyalkynyl)radicals of ring size C8 to C20;

D is oxygen, sulfur, $CH_2$, $CF_2$, or $N-R_2$;

F is alkyl, alkenyl, alkynyl, branched alkyl, branched alkenyl, branched alkynyl, cycloalkyl, bridged cycloalkyl, cycloalkenyl or cycloalkynyl radicals containing C1 to C20 carbon atoms;

$R_1$ and $R_2$ are independently hydrogen, alkyl, alkenyl, alkynyl, branched alkyl, branched alkenyl, branched alkynyl, cycloalkyl, bridged cycloalkyl, cycloalkenyl, bridged cycloalkenyl or cycloalkynyl radicals containing C1 to C20 carbon atoms, or any protecting group described in the book "Protecting Groups in Organic Synthesis" by Theodora Greene and Peter G. M. Wuts.

Another class of phosphocholine derivatives (Class III) having antifungal activity has the following structures:

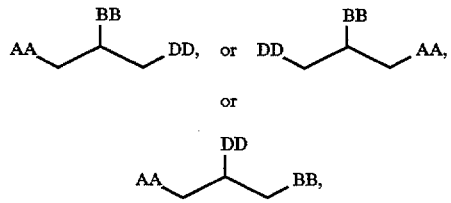

where AA, BB, DD are independent of each other, equal to each other, or interchanged as shown above, the central carbon atom can be either the R and S optical stereoisomer or a mixture of R and S stereoisomers, and where AA, BB, and CC DD defined as follows:

where AA, is A–J with A being attached to the carbon atom of the three carbon central unit and J is defined below;

BB is B–Y, with B being attached to the carbon atom of the three carbon central unit and Y is defined below:

DD is

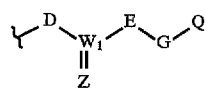

where W, E, G and Q are defined below;

A is oxygen, sulfur, $CH_2$, $CF_2$ or $N-R_1$;

B is oxygen, sulfur, $CH_2$, $CF_2$ or $N-R_2$;

D is oxygen, sulfur, $CH_2$, $CF_2$ or $N-R_3$;

Y is alkyl, alkenyl, alkynyl, poly(alkenyl), poly(alkynyl), or poly(alkenoalkynyl) radicals comprised of C1 to C20 carbon atoms chain lengths, or alkanoyl, alkenoyl, alkynoyl, poly(alken)oyl, poly(alkyn)oyl or poly(alkenoalkyn)oyl radicals comprised of C2 to C20 chain lengths or alkyloxy, alkenyloxy, alkynyloxy, poly(alkenyl)oxy, poly(alkynyl)oxy, poly(alkenoalkynyl)oxy radicals comprised of C1 to C20 carbon atoms;

J is a furanose or pyranose radical of the type:

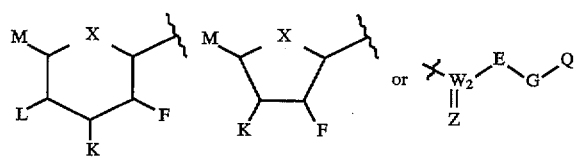

where X is oxygen, sulfur, $CH_2$, $CF_2$ or $N-R_4$;

F, K, L and M are independently hydrogen, hydroxyl, protected hydroxyl (as described in the book "Protecting Groups in Organic Synthesis" by Theodora Greene and Peter G. M. Wuts), alkyloxy, thiol, alkylthio, arylthio, alkylsulfonyl, arylsulfonyl, amino, ammonium, alkylamino, alkylammonium, dialkylamino, dialkylammonium, trialkylamino, trialkylammonium where the alkyl chain on nitrogen is comprised of C1 to C20 carbon atoms; or alkyl, alkenyl, or alkynyl radicals comprised of C1 to C20 carbon atoms.

Z is oxygen or sulfur

E is oxygen, sulfur, $CH_2$ $CF_2$ or $N-R_5$;

G is alkyl, branched alkyl, cycloalkyl or bridged cycloalkyl radicals of C1 to C20 chain lengths;

Q is halogen, hydroxyl, protected hydroxyl utilizing any protecting groups described in the book "Protecting Groups in Organic Synthesis" by Theodora Greene and Peter G. M. Wuts, O-arylsulfonyl-, O-alkylsulfonyl- or O-(perfluoroalkyl)sulfonyloxy, amino, ammonium, alkylamino, alkylammonium, dialkylamino, dialkylammonium, trialkylamino, trialkylammonium where the alkyl chains on nitrogen are C1 to C20, or $Q=NR_1R_2R_3$, where $R_1$, $R_2$, or $R_3$ can independently or together be a mixture of alkyl groups of C1 to C20 in chain length and a protecting group described in the book "Protecting Groups in Organic Synthesis" by Theodora Green and Peter G. M. Wuts, and $R_1$ can equal $R_2$, $R_2$ can equal $R_3$, or $R_1$ can equal $R_3$ which can equal $R_3$;

$R_1$, $R_2$, $R_3$, $R_4$ and $R_5$ are independently alkyl, alkenyl, alkynyl, branched alkyl, branched alkenyl, branched alkynyl, cycloalkyl, bridged cycloalkyl, cycloalkenyl or cycloalkynyl radicals of C1 to C20 chain lengths, or any protecting group described in the book "Protecting Groups in Organic Synthesis" by Theodora Greene and Peter G. M. Wuts;

where $W_1$ and $W_2$ are P(—OR)(with R being phenyl, phenylmethyl, or negatively-charged oxygen), S=O, carbon, or sulfur, provided that if $W_1$ is not P(—OR) $W_2$ is P(—OR) and provided that if J is a furanose or pyranose radical then $W_1$ is P(—OR), A preferred subgroup of the above-described Class III of phosphocholine derivatives have the following structures:

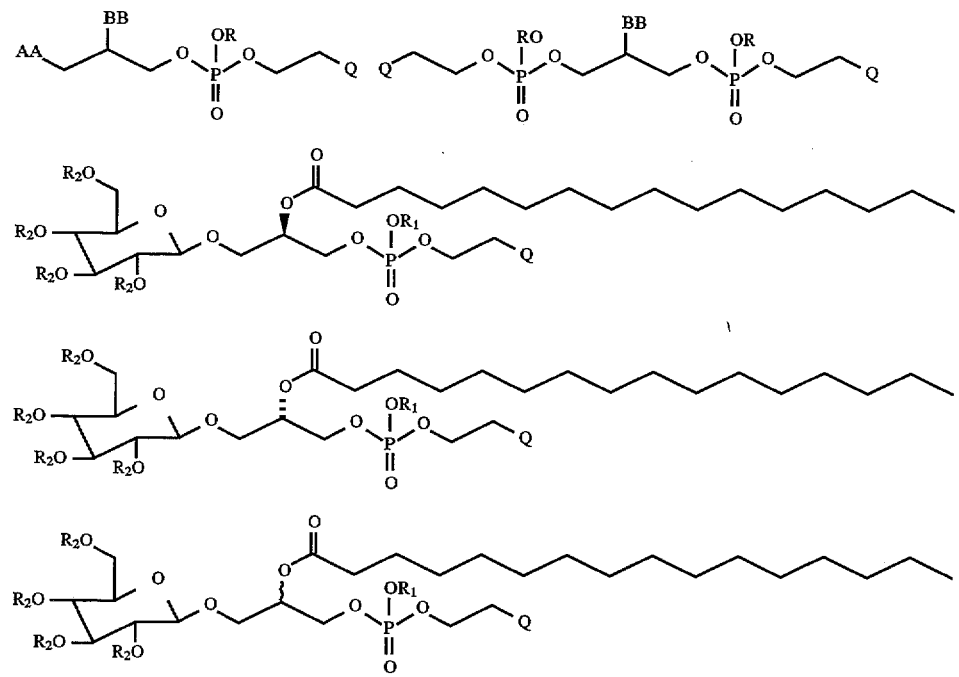

where $R_1$ is phenyl or phenylmethyl, hydrogen, or nil;

$R_2$ is hydrogen, phenylmethyl, or any protecting group described in the book "Protecting Group in Organic Synthesis" by Theodora Green and Peter G. M. Wuts which can be cleaved by hydrogenolysis;

AA, BB, and Q are as defined above where the central carbon atom of the three carbon unit is either the R optical isomer, the S optical isomer, or any mixture of the two optical isomers thereof;

Another preferred subgroup of the above-described Class III of phosphocholine derivatives have the following structures:

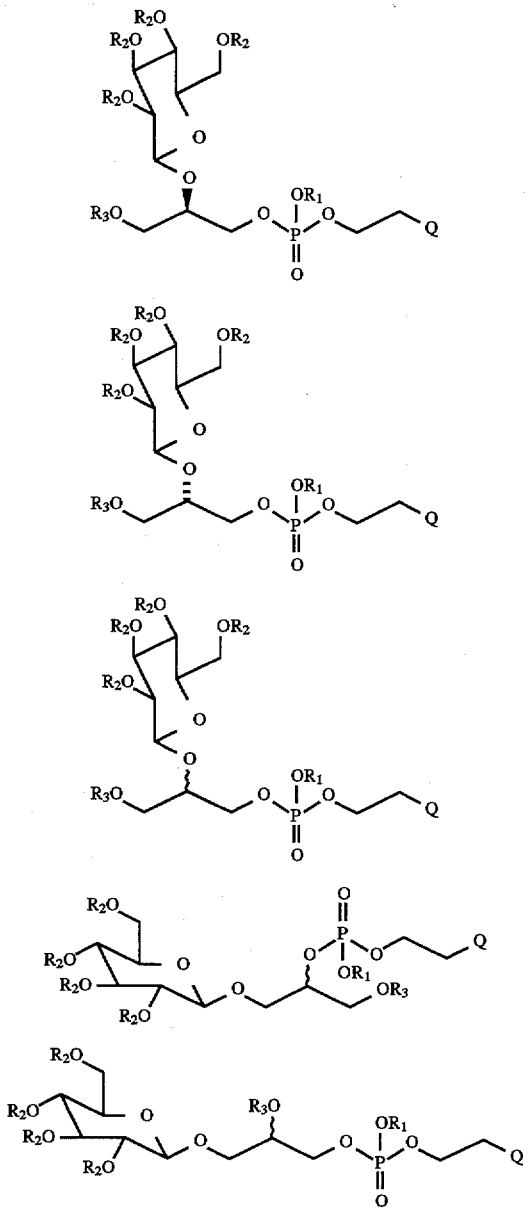

where $R_1$ is phenyl or phenylmethyl, hydrogen, or nil; $R_2$ is hydrogen, phenyl methyl or any protecting group described in the book "Protecting Groups in Organic Synthesis" by Theodora Greene and Peter G. M. Wuts which can be cleaved by hydrogenolysis;

$R_3$ is hydrogen or a protecting group as described in the book "Protecting Groups in Organic Synthesis" by Theodora Greene and Peter G. M. Wuts.;

where the central carbon atom of the three carbon unit is either the R optical isomer, the S optical isomer, or any mixture of the two optical isomers thereof; and Q is defined above.

Still another preferred subgroup of the above-described Class III of phosphocholine derivatives have the following structures:

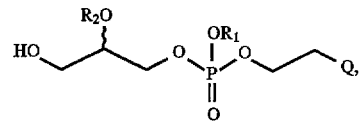

and

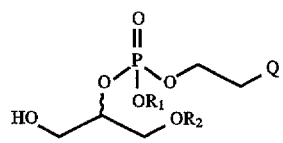

where $R_1$ is phenyl or phenylmethyl, hydrogen, or nil;

$R_2$ is a protecting group as described in the book "Protecting Groups in Organic Synthesis" by Theodora Greene and Peter G. M. Wuts, or hydrogen if $R_1$ is not hydrogen;

and Q is defined above.

We have further found a novel, generally applicable method for the synthesis of the above described broad classes of phosphocholine derivatives (Classes I, II and III).

4. BRIEF DESCRIPTION OF THE DRAWINGS

5. DETAILED DESCRIPTION OF THE INVENTION

Figure 1:
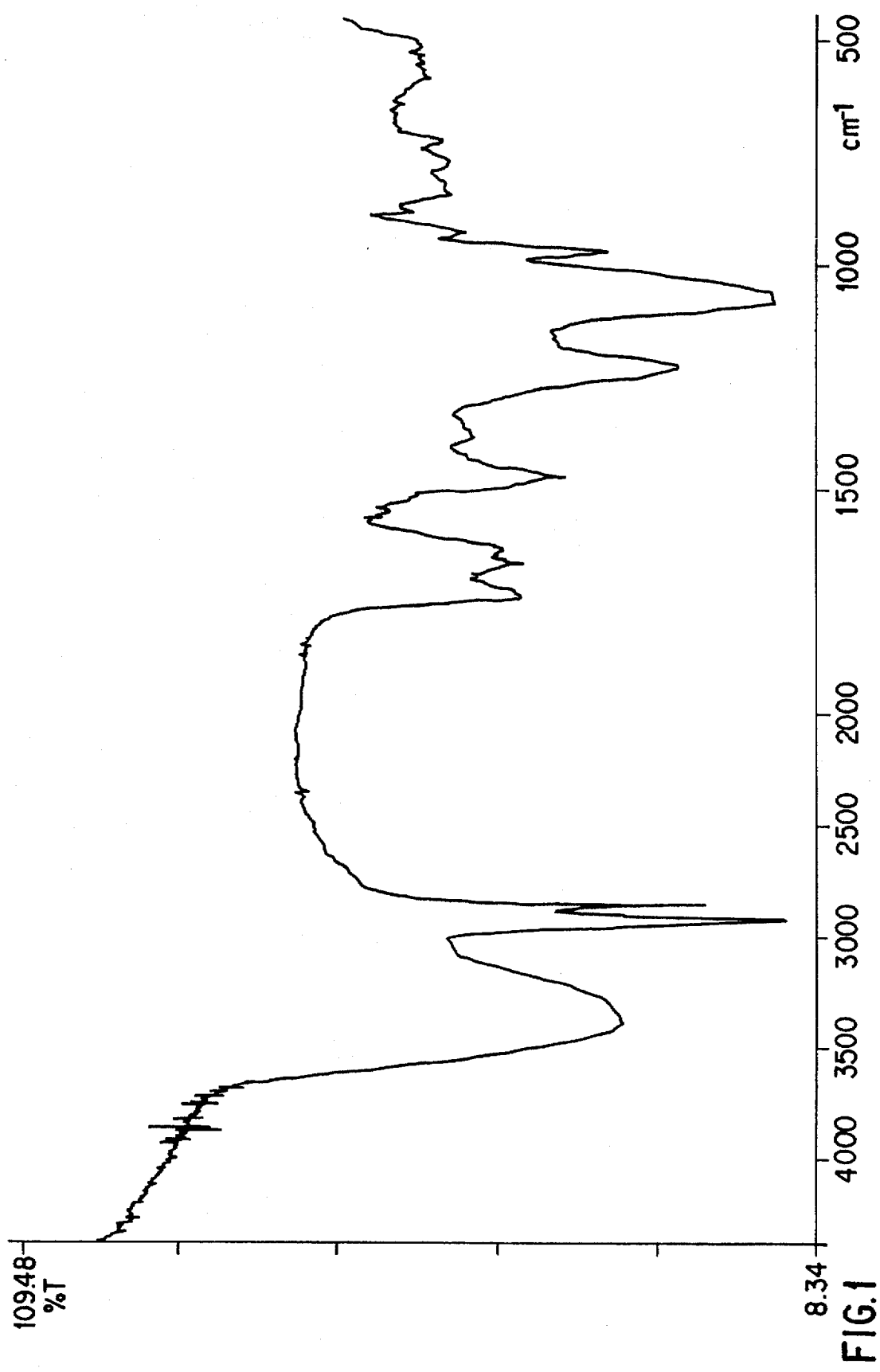
FIG. 1 is the FTIR spectrum of the composition comprising a phosphocholine derivative obtained from *Irlbachia alata*.

The glysosylated lysolecithins of the invention can be prepared by synthetic methods or by enzymatic methods. The phosphocholine derivatives can be prepared either by synthetic methods or by methods entailing extraction from plant materials.

5.1. Chemical Synthesis of Phosphocholine Derivatives

A wide variety of compounds having accessible alcoholic functionalities can be glycosylated following the classic Koenigs-Knorr methodology. Bochkov, A. F. and Zaikov. G. E., Chemistry of the O-Glycosidic Bond. Pergamon Press, 1979. As part of the synthetic route to phosphocholine derivatives with sugar, all but the anomeric hydroxyl group of the sugar to be introduced are protected either as esters or ethers, while the anomeric hydroxyl is being replaced by a halogen. The aglycon-sugar linkage is then formed via alcoholysis. Finally, the protective groups are selectively removed.

In the present invention, benzyl ethers or the benzilidine moiety are are the preferred protecting group, since they can be selectively removed by catalytic hydrogenation, while leaving the sensitive acyl-glycerol linkage intact. The glycosidation requires silver, mercury (Helferich modification), or cadmium salts as catalytic halogen abstractor, in the presence of a dehydrating agent (Timell, T. E., Can.J. Chem. 1964, 42, 1456; Dejter-Juszynsky, M. and Flowers, H. M., Carbohydr. Res. 1973, 30, 287; Marousek, V., Lucas, T. J., Wheat, P. E., and Schuerch, C., Carbohydr. Res. 1978, 60, 85), and with or without auxiliaries such as crown-ethers. (Knöchel, A. Ger, R., and Thiem, J. Tetrahedron Letters 1974, 551) More recent methodology makes use of the halogen-abstracting power of non-nucleophilic bases such as diisopropylethylamine and/or of molecular sieves in an anhydrous media. (Garegg, P. J. and Norberg, T., Carbohydr. Res. 1976, 52, 235) The following synthetic scheme is based on the latter reaction sequence:

methodology outlined above is also applicable to either 1-acyl or 2-acyl (1-acyl detailed above).

5.2. Enzymatic Preparation of 1 or 2 glycosylated lysolecithins

As an alternative to the synthetic sequence outlined above, an in vitro enzymatic glycosidation simulating the biosynthetic process will produce the desired compounds in comparable yields. The natural glycosidation catalysts are glycosyltransferases. These enzymes operate with uridinediphospho-glycosides (UDP-sugars) as substrates and ATP as the energy source. While the enzymes have to be prepared from fresh plant material, UDP-sugars, ATP, as well as the respective phosphocholine derivatives are commercially available. This synthesis has the advantage of

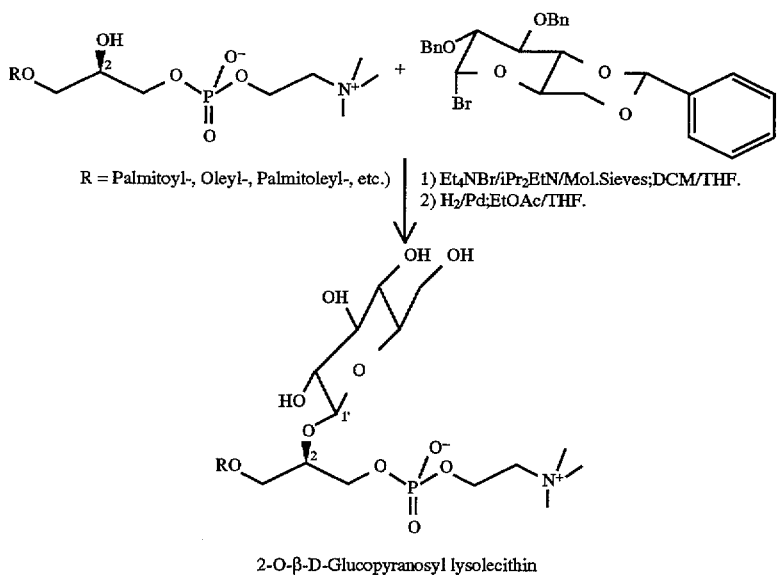

2-O-β-D-Glucopyranosyl lysolecithin

The synthetic two-step scheme outlined above can be conducted with commercially available materials. 2,3,4,6-Tetrabenzyl-2,3-dibenzyl-4,6-benzylidene-glucose can be converted into the 1-bromo- or 1-O-triflate compound by standard methodology. Leroux, J. and Perlin, A. S. Carbohydr. Res. 1976, 47, C8. The corresponding phosphocholine derivatives are available through AVANTI POLAR LIPIDS, Inc. All other reagents are available from ALDRICH. The being essentially a one-step process with the high selectivity and yields expected from an enzymatic reaction. The following scheme describes the preparation of a glucoside. Other transferases, not specific to glucose, could be applied in the preparation of glycosylated lysolecithins with other sugars as well:

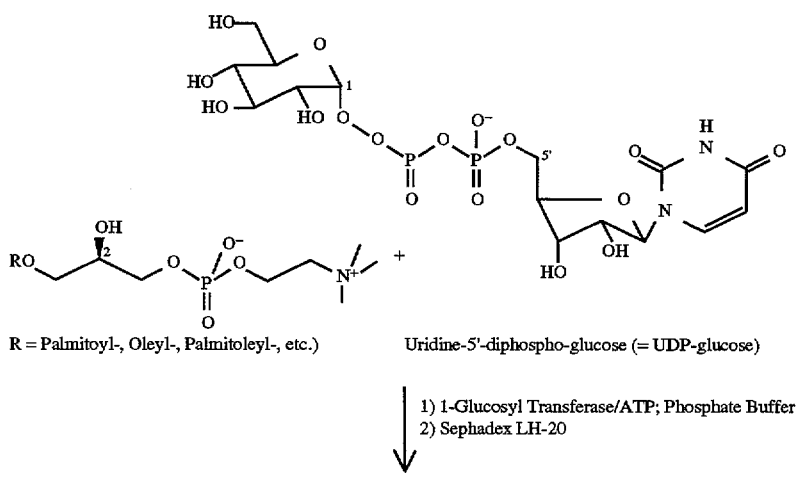

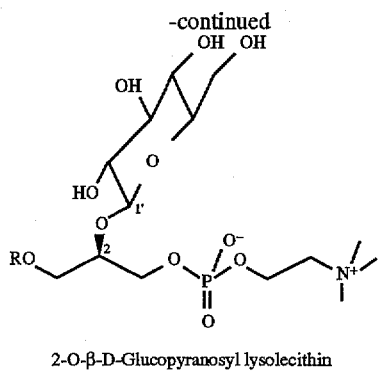

2-O-β-D-Glucopyranosyl lysolecithin

5.3. Total Synthesis of Phosphocholine Derivatives

A general synthetic method of synthesizing phosphocholine derivatives of the various structures described in section 3 is outlined as follows.

An alcohol is phosphorylated or glycosylated. The product is subsequently deprotected. The deprotected product is then alkylated or esterified to produce the phosphocholine derivatives. The general scheme for this outlined synthetic method is shown below.

The antifungal agent of phosphocholine derivatives in Class II can be administered intravenously in a range of about 0.1 to about 10 mg/kg.

The fungal agent of Class II can be administered intraperitoneally in a range of about 0.1 to about 10 mg/kg.

The fungal agent of Class II can be administered subcutaneously in a range of about 1 to about 20.

The fungal agent of Class II can be administered intramuscularly in a range of about 1 to about 20.

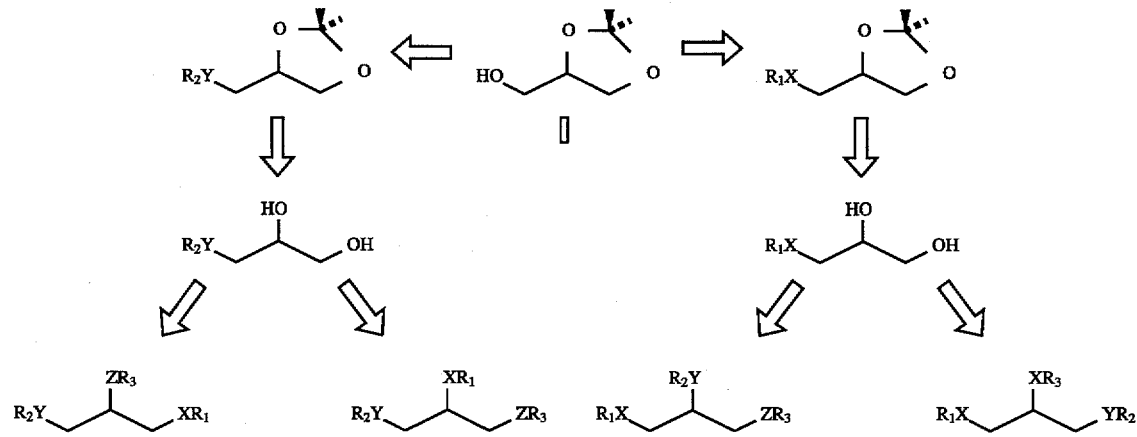

General Scheme for the Synthesis of Known and Novel Lysolecithins

Glycerol Derivative [] can be either the R or S optical isomer, racemic or a mixture of R and S isomers ⟹ Implies that a number of synthetic transformations are required $R_1$ = Sugar, carbocyclic sugar, functionalized sugar derivative, etc.
$R_2$ = Phosphate or phosphate isostere moiety
$R_3$ = alkyl, alkanoyl, alkenyl, alkenoyl, etc.
X, Y, and Z can be C, O, N, S independently or equal to each other

5.4. Methods of Use

The phosphocholine derivative in Classes I, II and III are all useful in treating fungal infection by the administration to a warm-blooded animal of a therapeutically effective amount of a phosphocholine derivative. The pharmaceutical composition comprising the phosphocholine derivative used for such administration may also contain pharmaceutically acceptable excipients and carriers.

Phosphocholine derivatives in Classes I and II are believed to be novel compositions.

In order to treat a fungal infection, the antifungal agent of Classes I, II and III may be administered to a warm-blooded animal intravenously, intraperitoneally, subcutaneously, intramuscularly, orally, topically, by aerosol, or combinations thereof.

The fungal agent of Class II can be administered orally in a range of about 5.0 to about 30 mg/kg.

The fungal agent of Class II can be administered topically in a range of about 5.0 to about 15% by weight.

The fungal agent of Class II can be administered by aerosol in a range of about 5.0 to about 30 mg/kg/day.

The above dosage ranges may need to be doubled for those phosphocholine derivatives in Class I and III with lower antifungal activity which are identical or similar to those in table 2 (see below).

6. Extraction of Phosphocholine Derivatives From Plants

Plants are not known to contain phosphocholine derivatives.

The general manner of chemical extraction from the plants can be summarized as follows.

The plant source material, such as the whole plant, the roots, leaves, stem and/or latex of the plant, is extracted with water and/or a water miscible solvent. The preferred solvents are alcohol of 1–3 carbon atoms or acetone. The aqueous extract is extracted with butanol. The butanol-soluble fraction is subjected to gel filtration (e.g., over Sephadex), reversed-phase column chromatography (e.g., C-8), or gel-permeation chromatography (e.g., divinyl benzene cross-linked gels) such as PL-GEL or membranes (e.g., an Amicon membrane) using water or water and a water miscible solvent, with or without a buffer, as the mobile phase. The water miscible solvent is preferably a 1–3 carbon alcohol, acetone or acetonitrile.

The useful phosphocholine derivatives containing compound is the fraction detected by NMR spectroscopy.

A specific member of the class of phosphocholine derivatives of the present invention is 2-palmitoyl-1-O-glycopyranosyllysolecithin shown below:

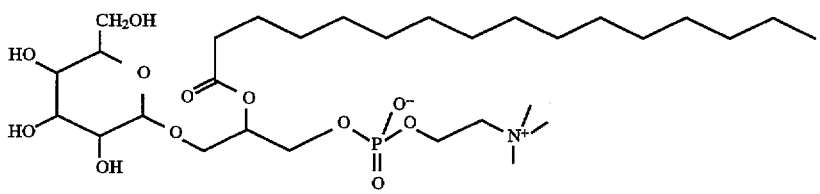

2-Palmitoyl-1-O-glucopyranosyllysolecithin

We have found that 2-palmitoyl-1-O-glucopyranosyllysolecithin is a relatively active antifungal agent similar in activity to L-a-Lysophosphatidyl inositol, discussed in Table 2 below.

We have found that one of the most active antifungal compounds has the following structure.

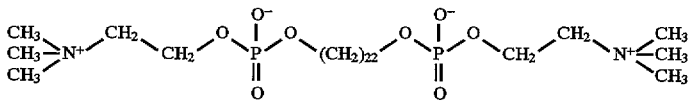

1,22-docosan diol bisphosphocholine ester.

6.1. Extraction

We have isolated by chemical extraction 1,22-docosan diol bisphosphocholine ester, the active antifungal compound contained in the plant *Irlbachia alata*. The leaves of *Irlbachia alata* were milled and 200 g of the milled leaves was extracted with 1L of dichloromethane/isopropanol (1:1 v/v) at room temperature for 24 hours. The extracted material was separated from the marc (i.e., residual of the plant after solvent extraction) and discarded. The marc was then extracted with 1.5L of isopropanol/water (1:1 v/v) at room temperature for 24 hours. The marc was separated from the extract and discarded. The isopropanol/water (1:1 v/v) soluble extract was partitioned between water and ethyl acetate. The ethyl acetate phase was separated and discarded. The water soluble phase, after extraction with n-butanol, was then discarded. The n-butanol phase was subjected to filtration over two Sephadex LH-20 gel columns using 90% aqueous ethanol (for first filtration) and 20% aqueous acetone (for second filtration) as the mobile phases. 1,22-docosandiol bisphosphocholine ester was collected from the early fractions of each gel filtration.

We believe that several related genera are the same and/or closely related to the genus Irlbachia, and would have similar medicinal properties. One species from a closely related genus, *Lisianthus nigrens* is used in Mexico. The leaves are applied as a poultice to treat fungal infections of the skin, feet, ankles and hands. A decoction of the root is also taken orally as a "bitter" and as a febrifuge. Another species *Lisianthus alatus* is considered to be the same as *Irlbachia alata*. Another species and genus of interest is *Chelonanthus alatus*. There are several uses described for *Chelonanthus alatus*, including oral decoctions to treat smallpox, fevers and for gastric disturbances.

6.2. Spectral Characteristics

Figure 2:
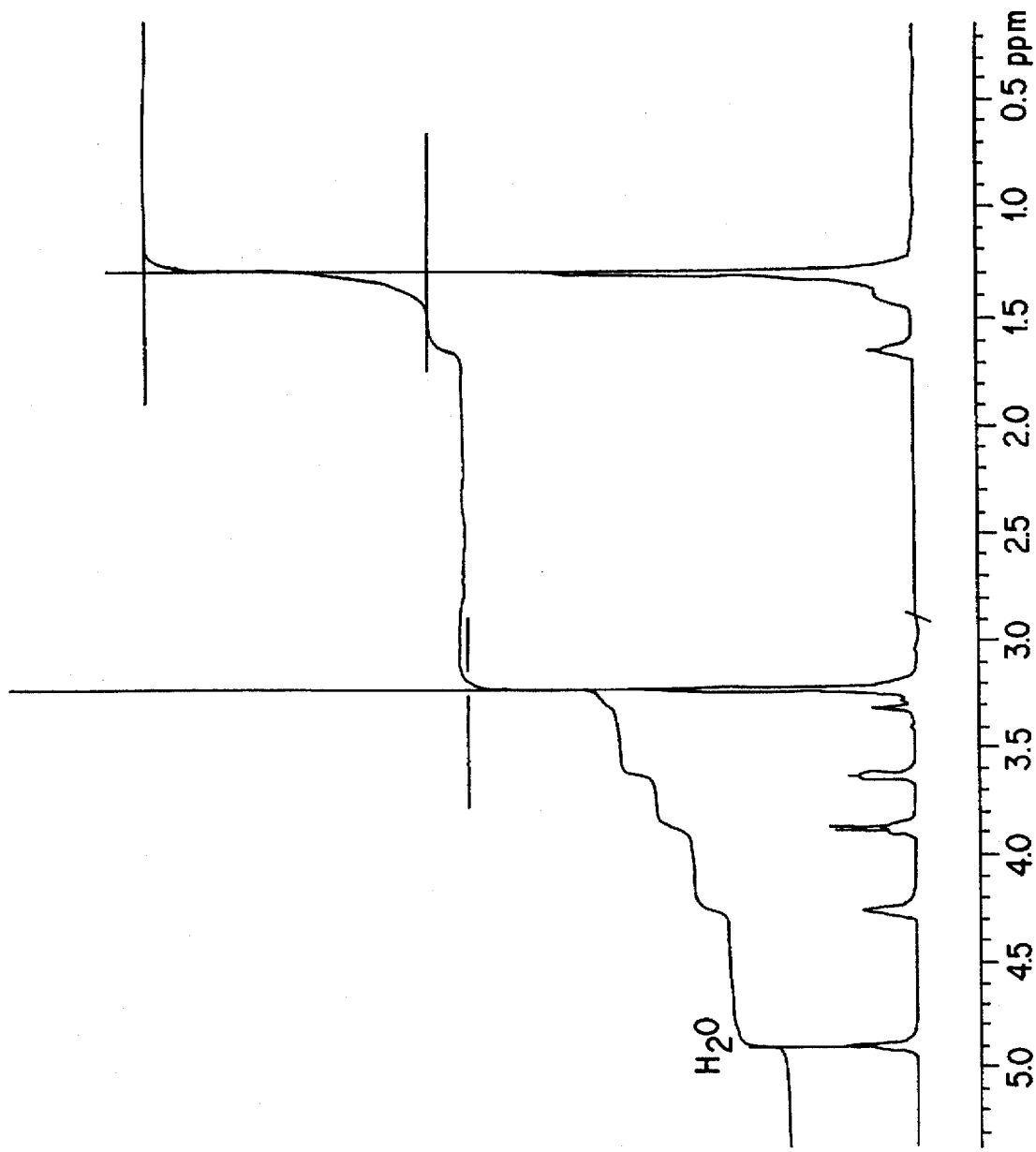
FIG. 2 is the proton NMR spectrum of the composition comprising a phosphocholine derivative obtained from *Irlbachia alata* in $D_2O$ at 400 mHz.
Figure 3:
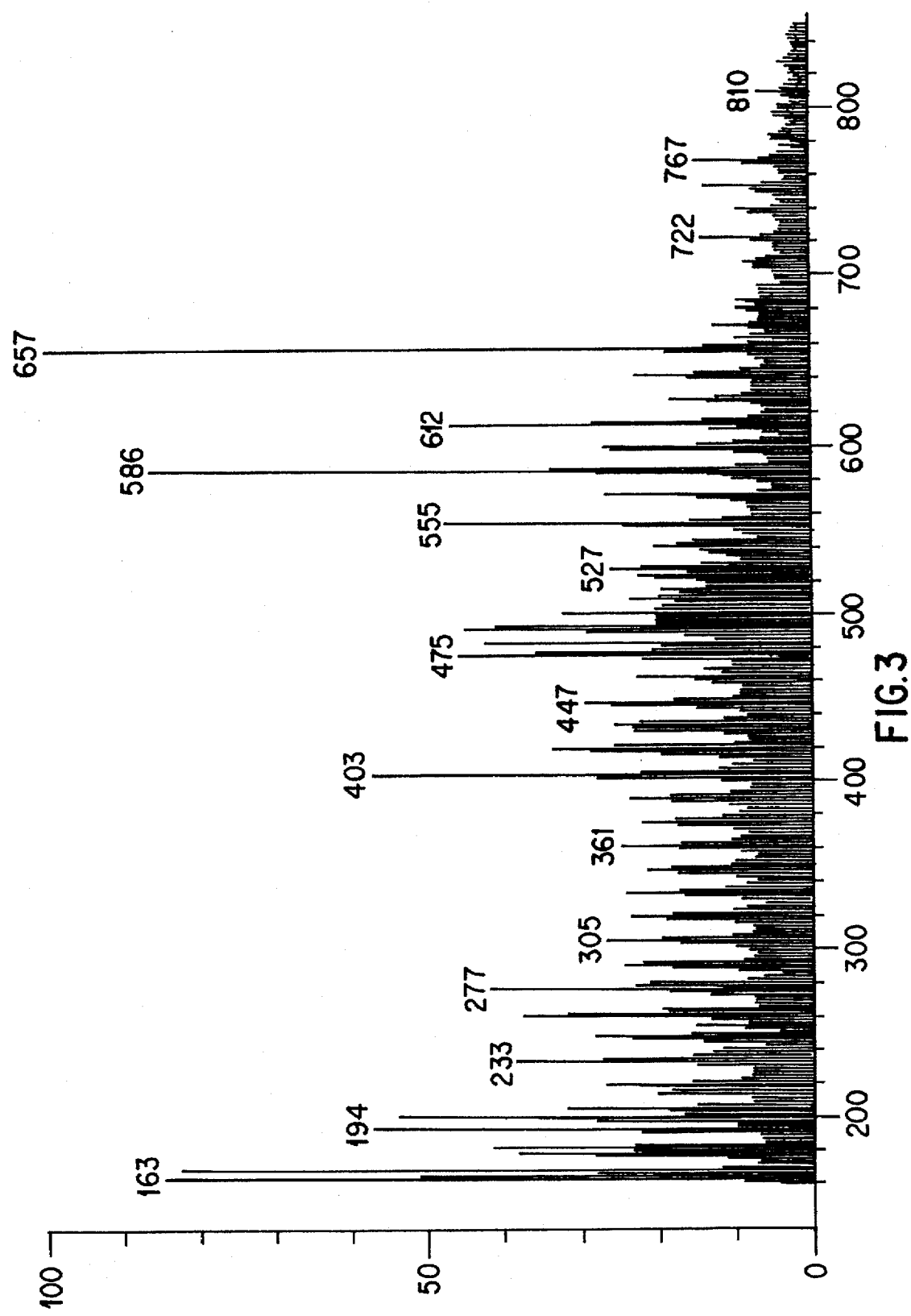
FIG. 3 is the FAB/MB mass spectrum of the composition comprising a phosphocholine derivative obtained from *Irlbachia alata*.

The isolated phosphocholine derivative fraction containing 1,22-docosandiol bisphosphocholine ester has the characteristic IR, proton NMR and FAB mass spectra shown in FIGS. 1, 2 and 3, respectively.

The IR spectrum has peaks at approximately 1060, 1220, 1475, 1600–1700, 2850, 2950 and 3400 cm$^{-1}$.

The $^1$H NMR spectrum has major peaks at δ 1.2, 1.4, 1.7, 3.1, 3.5, 3.7 and 4.3.

The FAB/MB mass spectrum has major peaks (>40%) at m/z 657, 612, 587, 586, 555, 493, 491, 475, 403, 277, 233, 201, 194, 179, 168, 165 and 163.

The high resolution mass spectrum (FAB$^+$) has a molecular ion at 673.4669 amu.

6.3. Total Synthesis of 2-palmitoyl-1-O-glucopyranosyllysolecithin Experimental Section General Tetrahydrofuran (THF) was distilled from potassium/benzophenone; benzene, triethylamine, and methylene chloride, N-methylmorpholine, and benzyl alcohol were distilled from calcium hydride; 2-bromoethylphosphorodichloridate was prepared according to the procedure reported by Baumann et al Lipids, 17, 453 (1982) and was freshly distilled prior to use; trifluromethanesulfonic anhydride was freshly distilled under inert atmosphere; O-α-D-(Glucopyranosyl) trichloroacetimidate was prepared by the method of Schmidt. (a) R. R. Schmidt, J. Michael, *Angew. Chem. Int. Ed Engl.* (1980), 19, 731; (b) R. R. Schnmidt, J. Michael, *Tetrahedron Lett.* (1984), 25, 821. Anhydrous dimethylformamide (DMF) was obtained from Aldrich. S-(+)-1,2-O-isopropylidene glycerol and R-(−)-1,2-O-isopropylidene glycerol were obtained from Lancaster. 2,3,4,6-Tetra-O-benzyl-D-glucopyranose was obtained from Sigma. Preparative thin layer chromatography plates was performed on Whatman 2000 μTLC silica gel plates. Flash column chromatography was performed on Whatman 230–400 mesh silica gel using nitrogen pressure. $^1$H and $^{13}$C NMR were provided by using a Varian 400 MHz spectrometer with chloroform as an internal reference unless otherwise noted. NMR shifts were expressed in ppm downfield from internal tetramethylsilane. Carbon 13 multiplicities as determined by DEPT experiments are reported in parentheses following the chemical shift value according to the following format: (0) for quaternary carbon, (1) for methine carbon, (2) for methylene carbon, and (3) for methyl carbons. NMR assignments were determined on the basis of COSY, HMQC, and HMBC and DEPT experiments performed on selected intermediates. NMR coupling constants are reported in Hertz. Melting points were determined using a Buchi model 535 melting point apparatus and are uncorrected.

The synthetic routes for the total synthesis of 2-palmitoyl-1-O-glucopyranosyllysolecithin are outlined in the following diagrams and detailed in the subsequent discussion that refer to these diagrams.

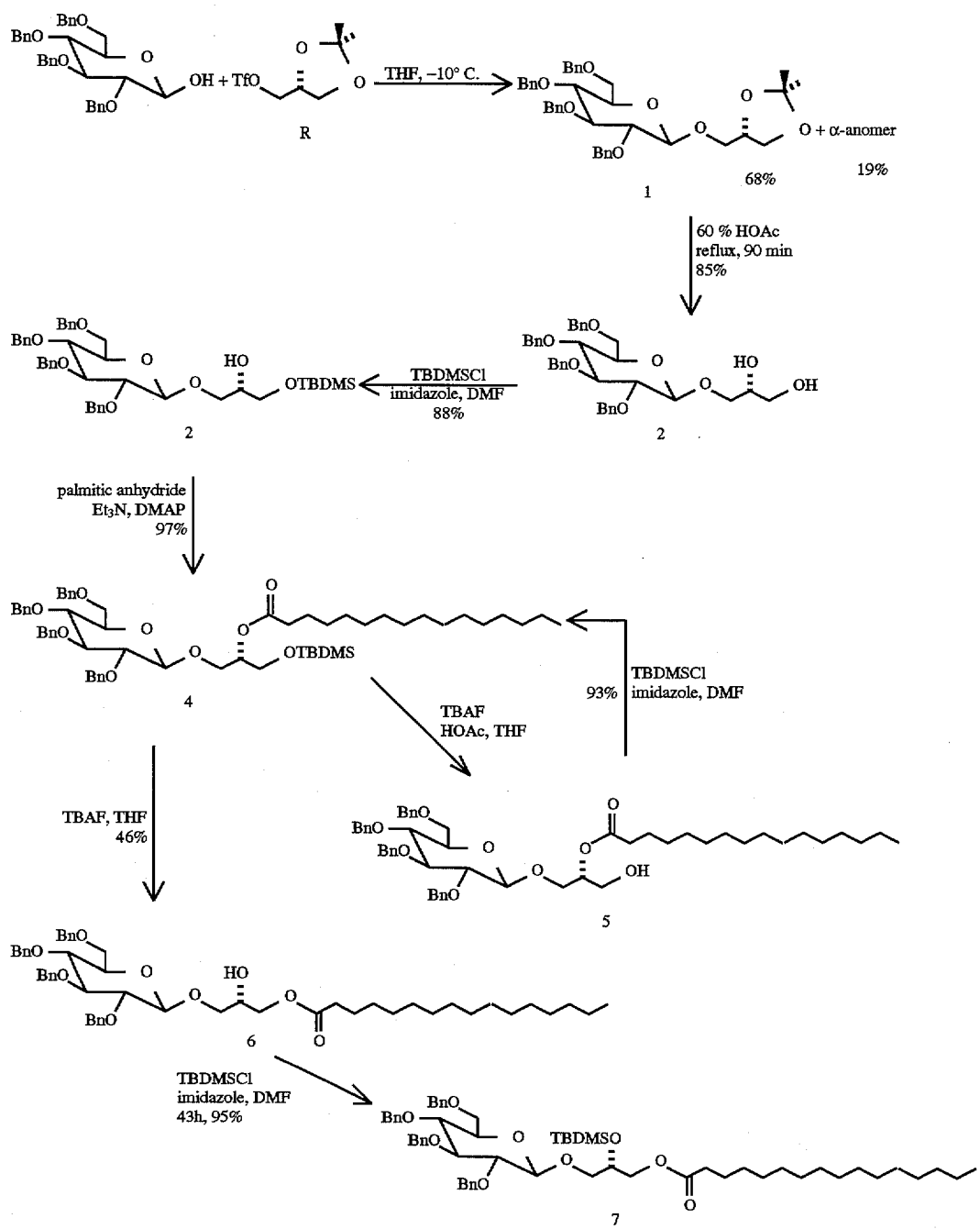

Scheme 1. Synthesis of the (S) SP-19501: Preparation of the Regioisomeric Glycerol Alcohols Scheme 2. Synthesis of the (R) SP-19501: Preparation of the Regioisomeric Glycerol Alcohols
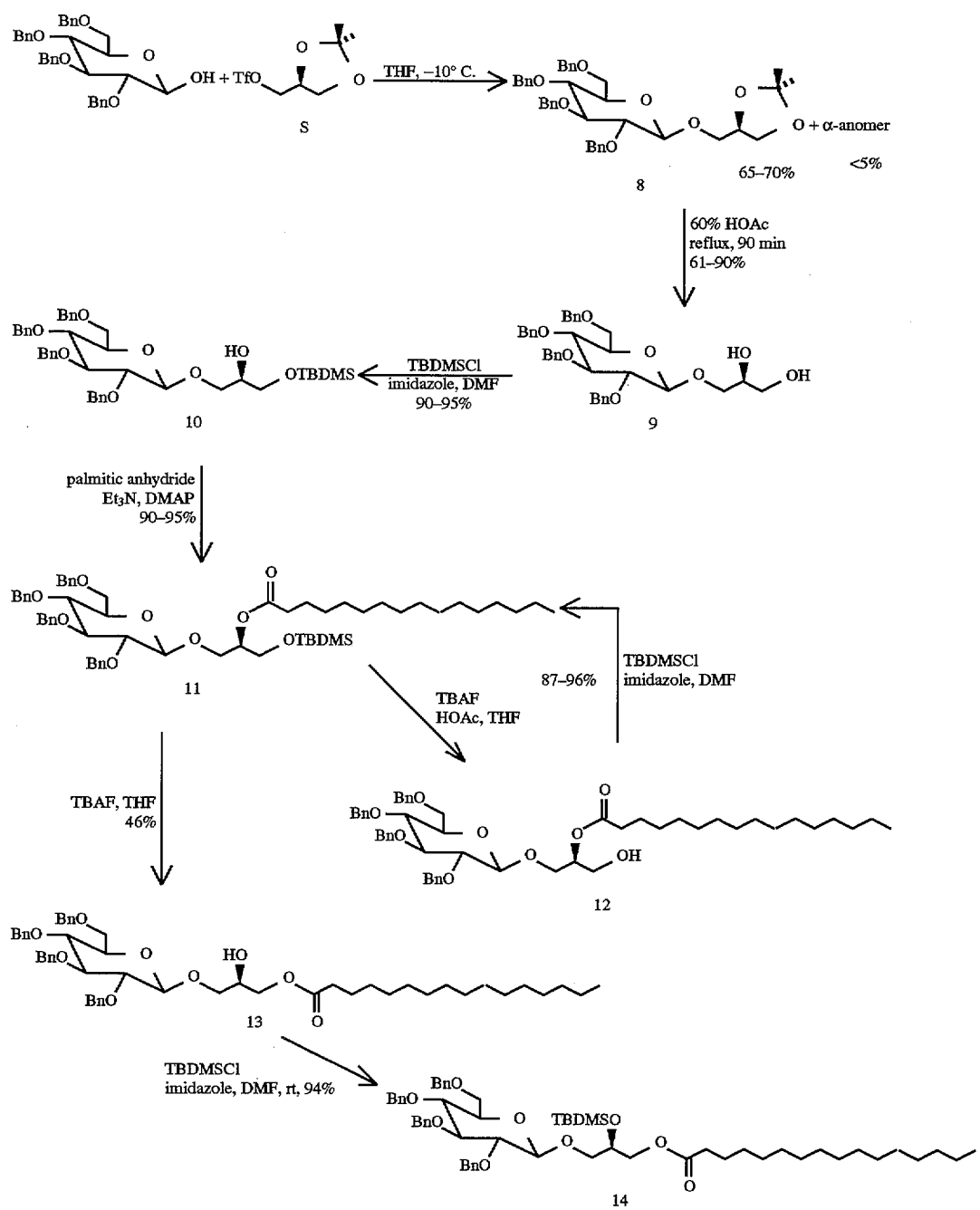

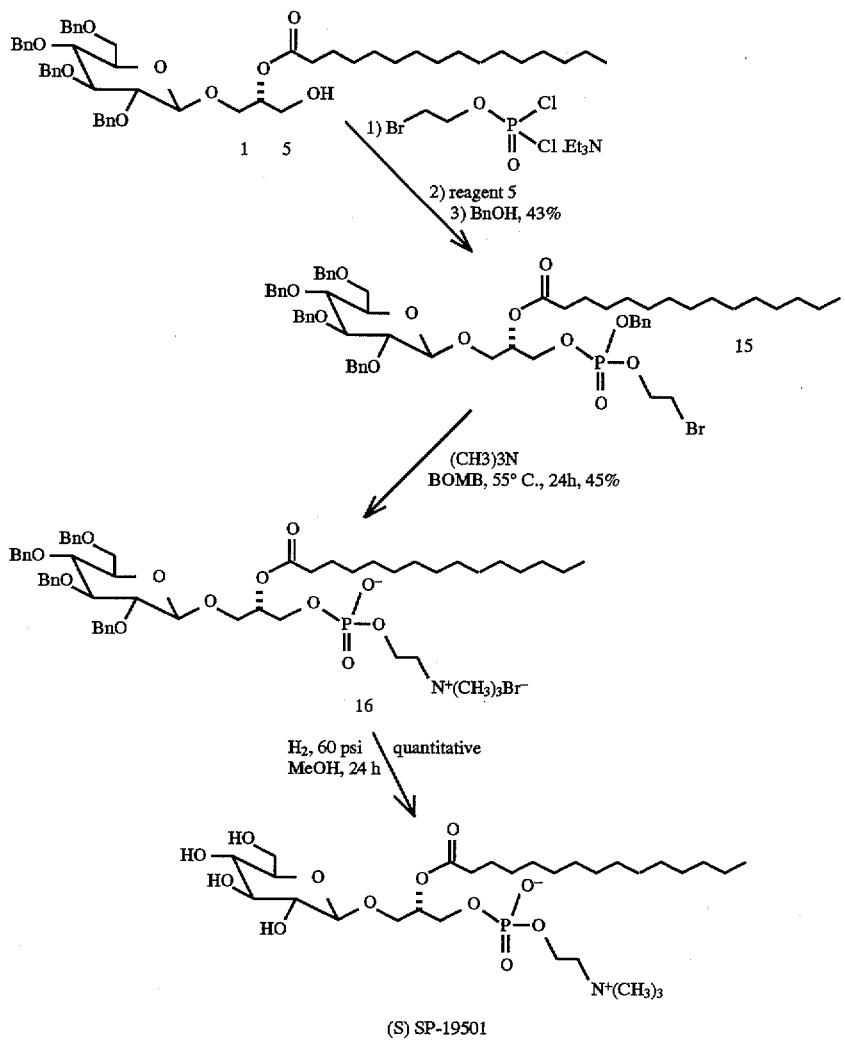
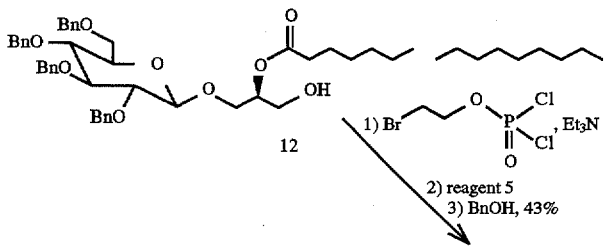

-continued
Scheme 4. Synthesis of (R) SP-19501
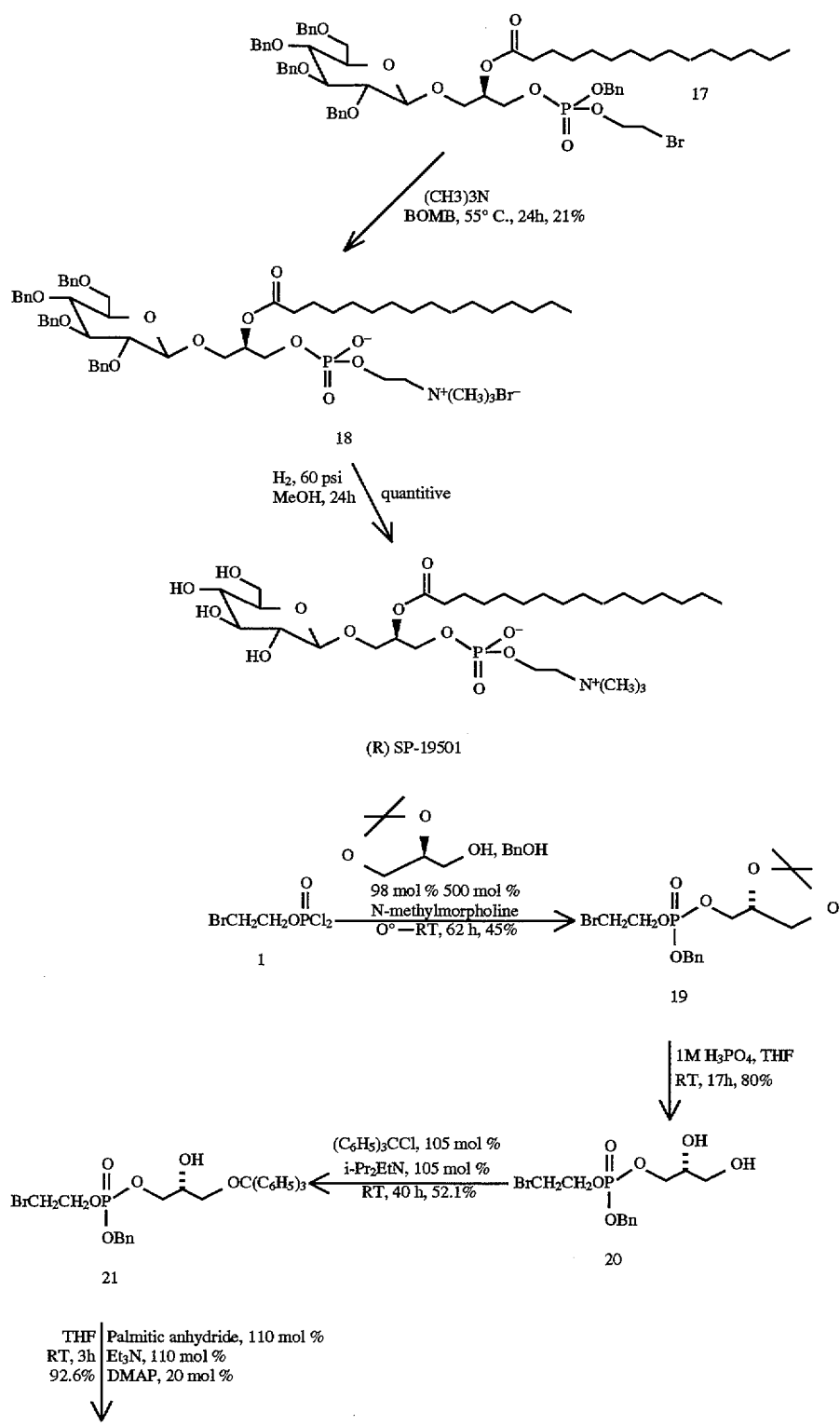
(R) SP-19501

Scheme 4. Synthesis of (R) SP-19501

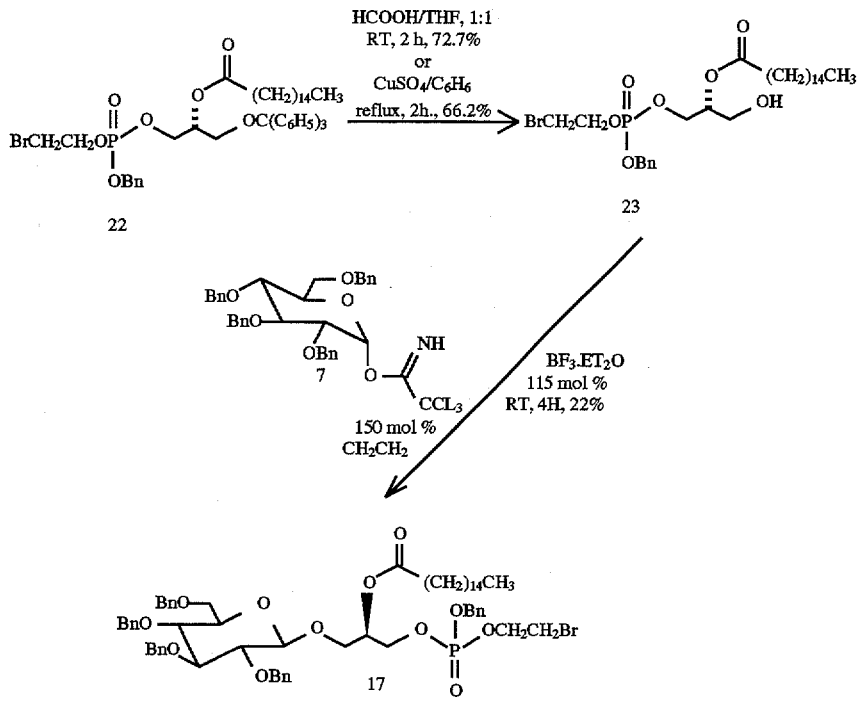

(R) 2,3-O-Isopropylidene-1-O-trifluromethylsulfonyl—glycerol.

A nitrogen-purged 250-mL three-necked roundbottomed flask fitted with a thermometer, stopper, and septum was charged with S-(+)-1,2-O-isopropylidene glycerol (1.0 g, 7.6 mmol) dissolved in benzene (75 ml). Triethylamine (1.25 mL, 9.0 mmol) was injected into the solution, and the reaction mixture was chilled until a cloudy solution appeared. Trifluoromethanesulfonic anhydride (1.25 mL, 7.6 mmol) was then added, and the reaction was stirred for 30 minutes with the temperature maintained at 5° C. The solution was then filtered through a bed of silica. The filtrate was concentrated under reduced pressure at 30° C. to give an orange/brown oil (1.84 g, 7.0 mmol) in 92% yield which was used directly for the next step.

(2R) [1-O-(2,3,4,6-Tetra-O-benzyl-β-D-glucopyranosyl)-2,3-O-isopropylidene]glycerol 1

2,3,4,6-Tetra-O-benzyl-D-glucopyranose (100 g, 0.182 mol) was dissolved in THF (1.4 L) and chilled to −10° C. in a nitrogen-purged 3-L three-necked morton flask fitted with a thermometer, stopper, and mechanical stirrer. Sodium hydride 60% in oil (16.1 g, 0.403 mol) was added in 4 increments over 10 minutes, and the solution was stirred for 30 minutes. (R) 2,3-O-Isopropylidene-1-O-trifluoromethylsulfonylglycerol (60.0 g, 0.227 mol) dissolved in THF (500 mL) was then dropped via an addition funnel into the reaction mixture over a 30 minute period. The solution was stirred at −10° C. for 7 hours. Methanol (200 mL) was added dropwise to quench excess sodium hydride, the resulting brown solution was rotary evaporated under reduced pressure and then the residue redissolved in chloroform (750 mL). The organic layer was washed with water (2×750 mL). The combined aqueous layers were washed with chloroform (3×500 mL). Organic layers were pooled and rotary evaporated under reduced pressure to give a white solid which contained both α and β-epimers of the desired product. The solid was triturated with diethyl ether to give a white solid of purely β—product and a mother liquor which contained α and β-epimers. The mother liquor was concentrated and flash chromatographed (silica gel, 20% ethyl acetate/hexane). Yield of the solid white β-epimer product (81 g, 0.123 mol) was 68%, mp 91°–91.7° C. (lit 83°–84° C.);$^1$H-NMR (CDCl$_3$) δ7.4–7.29 (m, 18H), 7.20 (m, 2H), 4.96 (d, 2H J=10.8), 4.84 (t, 2H, J=10.8), 4.75 (d, 1H, J=10.8), 4.65 (d, 1H, J=12.4), 4.6–4.54 (overlapping dd, 2H, J=12H, J=10.4), 4.46 (d, 1H, J=7.2, H$_1$'), 4.38 (p, 1H, H$_2$), 4.12–4.02 (m, 2H, H$_{1a}$, H$_2$), 3.89 (pseudo t, 1H, J=7.2, H$_{1b}$), 3.79–3.6 (m, 5H), 3.50 (pseudo t, 2H), 1.46 (s, 3H), 1.40 (s, 3H); $^{13}$C-NMR (CDCl$_3$) δ138.529 (0), 138.370 (0), 138.066 (0), 138.013 (O), 128.432, 128.409, 128.129 ,128.015, 127.901, 127.810, 127.734, 127.666, 109.399 (0), 103.824 (C$_1$'), 84–631 (C$_3$'), 82.120 (C$_2$'), 77.713 (C$_4$'), 75.748 (2), 75.058 (2), 74.891, 74.853, 74.315 (2), 73.495 (C$_1$), 70.317 (2), 68.762 (C$_6$'), 66.896 (C$_3$), 26.880 (3), 25.386(3). Yield of the colorless, oily α-epimer (23 g, 0.035 mol) was 19%; $^1$H NMR (CDCl$_3$) δ7.4–7.24 (m, 18H), 7.14 (m, 2H), 4.98 (d, 1H, J=10.8), 4.88–4.78 (m, 3H), 4.67 (d, 1H, J=12), 4.62 (d, 1H, J=11.6), 4.47 (d, 2H J=11.6), 4.37 (t, 1H, J=6.4), 4.07 (pseudo pentet, 1H), 3.96 (t, 1H, J=8.8), 3.8–3.54 (m, 9H), 1.43 (s, 3H), 1.37 (s, 3H); $^{13}$C NMR (CDCl$_3$) δ138.764 (0), 138.203 (0), 138.165 (0), 137.816 (0), 128.440, 128.387, 128.364, 128.030, 127.947, 127.916, 127.886, 127.696, 127.590, 109.422 (0), 97.482(C$_1$'), 81.885(1), 79.890 (1), 77.508 (1), 75.703 (2), 75.088 (2), 74.535 (1), 73.457 (2), 73.108 (2), 70.279 (1), 69.020 (2), 68.314 (2), 67.040 (2), 26.827 (3), 25.424 (3).

(2R) 1-O-(2,3,4,6-Tetra-O-benzyl-β-D-glucopyranosyl)-glycerol 2.

A 5-L three-necked morton flask fitted with a mechanical stirrer, condenser, and stopper was charged with compound 1 (50 g, 76.2 mmol) in 60% aqueous acetic acid (2.5 L). The acidic solution was refluxed for 1.5 hours at 103° C. and then cooled to room temperature. Distilled water (1.5 L) was added to the solution causing precipitation of a white solid. The acidic solution was extracted with methylene chloride (4×1 L) which was subsequently neutralized with sodium bicarbonate solution and concentrated to a white solid. Trituration with diethyl ether gave white product. The remaining mother liquor was flash chromatographed (silica gel, 50% ethyl acetate/hexane) to give white solid product. The combined yield (61.9 g, 0.101 mol) was 83%, mp 101.5°–102.4° C. (lit 76°–78° C.); $^1$H NMR (CDCl$_3$) δ0.40–7.26 (m, 18H), 7.19 (t, J=3.5, 2H), 5.0–4.7 (m, 5H), 4.64–4.5 (m, 3H), 4.46 (d, 1H, J=8.0, H$_1$'), 4.0–3.60 (m, 11H, H$_1$'s, H$_2$, H$_3$, H$_3$', H$_{6b}$', H$_{6a}$', H$_4$', H$_5$', H$_2$, '), 2.55 (s, 2H, OH's); $^{13}$C NMR (CDCl3) 38.529 (0), 138.332 (0), 137.952 (0), 137.740 (0), 128.531, 128.550, 128.478, 128.189, 128.114, 128.091, 127.931, 127.871, 127.749, 104.279 (C$_1$'), 84.654 (C$_3$'), 82.158 (C$_2$'), 77.819 (C$_4$'), 75.779 (2), 75.081 (2), 75.028 (2), 74.527 (C$_5$'), 73.571 (2), 72.207 (C$_1$), 71.204 (C$_2$) 68.883, (C$_6$'), 63.353 (C3).

(2S) [1-O-(2113,4,6-Tetra-O-benzyl-β-D-glucopyranosyl)-3-O-tert-butyldimethylsilyl] glycerol 3

. In a nitrogen-purged 100-mL round-bottomed flask fitted with a septum was dissolved diol 2 (9.0 g, 14.7 mmol), imidazole (2.05 g, 30.2 mmol), and t-butyl dimethylsilyl-chloride (2.28 g, 15.1 mmol) in anhyd DMF (45 mL). The reaction mixture was stirred under nitrogen for 2.5 days, transferred to a 1-L separatory funnel, and methylene chloride (250 mL) and water (250 mL) were added. The aqueous layer was extracted with methylene chloride (2×250 mL) and then the combined organic layers were washed with water (2×100 mL). After drying and concentration, purification by flash chromatography (silica gel, 33% ethyl acetate/hexane) gave a colorless oil (9.2 g, 12.6 mmol) in 88% yield; $^1$H NMR (CDCl$_3$) δ7.48–7.3 (m, 18H), 7.25–7.21 (m, 2H), 5.00 (d, 2H, J=11.2), 4.89 and 4.88 (overlapping doublets, 2H, J=10.8, J=10.4), 4.83 (d, 1H, J=11.2), 4.67 (d, 1H, J=12.4), 4.60 and 4.59 (overlapping doublets, 2H, J=12.4, J=10.8), 4.50 (d, 1H, J=7.6 H$_1$'), 4.06–3.92 (m, 2H), 3.9–3.62 (m, 7H), 3.6–3.52 (m, 2H), 3.04 (s, 1H, OH), 0.978 (s, 9H), 0.142 (s, 6H); $^{13}$C NMR (CDCl$_3$) δ188.552 (0), 138.385 (0), 138.005 (0), 137.960 (0), 128.455, 128.440, 128.121, 128.060, 127.931, 127.863, 127.772, 127.734, 127.696, 104.377 (C1'), 84.692 (C3'), 82.219 (C2'), 77.804 (C4'), 75.771 (2), 75.073 (2), 74.959, (2), 74.717 (C5'), 73.541 (2), 73.078 (2), 71.060 (C2), 68.785 (C6'), 63.998 (C3), 25.970 (3), 18.668 (0), –5.299 (3).

(2S) [1-O-(2,3,4,6-T6tra-O-benzyl-β-D-glucopyranosyl)-2-O-palmitoyl-3-O-t-butyldimethylsilyl] glycerol 4

A nitrogen purged 500-mL round-bottomed flask fitted with a septum was charged with compound 3 (9.3 g, 12.8 mmol) and palmitic anhydride (6.94 g, 14.0 mmol) in dry THF (200 mL). Dimethylaminopyridine (316 mg, 2.6 mmol) and triethylamine (2.04 mL, 14.7 mmol) were added, and the reaction was stirred under nitrogen for 12 h. The mixture was then transferred to a 2-L separatory funnel, and diethyl ether (500 mL) and water (500 mL) were added. The aqueous layer was filtered through Whatman No. 1 paper and extracted with diethyl ether (2×500 mL). After drying over magnesium sulfate, the combined organic layers were concentrated and purified by flash chromatography (silica gel, 14% ethyl acetate/hexane) to give a light yellow oil (12.1 g, 12.5 mmol) in 97% yield; $^1$H NMR (CDCl$_3$) δ7.40 (br. s, 20H), 5.15 (5, 1H), 4.98 (t, 2H), 4.84 (t, 2H), 4.76 (d, 1H), 4.67 (d, 1H), 4.59 (dd, 2H), 4.52 (d, 1H), 4.13(dd, 1H), 3.84 (m, 6H), 3.67 (dd, 2H), 3.49 (t, 2H), 2.32 (t, 2H), 1.61 (m, 2H), 1.25 (br. s, 24H), 0.98 (s, 9H), 0.97 (s, 3H), 0.14 (s, 6H). $^{13}$C NMR (CDCl$_3$) δ73.280, 138.597, 138.438, 138.127, 138.096, 128.379, 128.356, 128.333, 128.083, 127.977, 127.863, 127.780, 127.605, 127.582, 103.831, 84.556, 81.984, 77.721, 75.695, 75.020, 74.876, 74.603, 73.488, 72.904, 68.754, 67.821, 61.661, 34.428, 33.950, 31.941, 29.717, 29.687, 29.649, 29.619, 29.497, 29.459, 29.384, 29.300, 29.148, 25.826, 24.953, 22.716, 18.268, 14.159, –5.375.

(2R) [1-O-(2,3,4,6-Tetra-O-benzyl-β-D-glucopyranosyl)-2-Opalmitoyl] glycerol 5

Procedure A Compound 4 (34.0 g, 35.1 mmol) was dissolved in THF (1.4 L) in a 3-L three-necked Norton flask fitted with a mechanical stirrer, thermometer, and a 500-mL addition funnel. The solution was chilled to 0° C., and a solution of tetrabutylammonium fluoride (TBAF)(520 mL, 1.0M in THF) which was buffered to pH=6.5 with acetic acid was added dropwise through the addition funnel. The reaction mixture was stirred for 11 h at 0° C., left to sit at –15° C. for 12 h, and stirred again for 4 h at rt. Water (100 mL) was added, and the solution was concentrated to 200 mL of solution. The concentrate was redissolved in methylene chloride (750 mL) in a 3-L separatory funnel and washed with water three times (750 mL, 2×500 mL). The combined aqueous layers were extracted with diethyl ether (500 mL). The combined organic layers were concentrated to give a red oil which was purified by flash chromatography (silica gel, 33–40% gradient of ethyl acetate/hexane). A white solid (28.0 g, 32.8 mmol) was obtained in 93% yield. $^1$H NMR (CDCl$_3$) δ 7.36 (br. s, 20H), 5.06 (t, 1H), 4.96 (dd, 2H), 4.84 (dd, 2H), 4.75 (d, 1H) 4.59 (m, 2H), 4.53 (dd, 1H), 4.45 (dd, 1H), 4.14 (m, 2H), 3.91 (m, 2H), 3.78 (m, 6H), 2.80 (s, 1H), 1.64 (m, 2H), 1.27 (br. s, 26H), 0.90 (t, 3H).

Procedure B Compound 4 (500 mg, 0.52 mmol) was dissolved in THF (20 mL) in a 100-mL three-necked round-bottomed flask fitted with two stoppers and a septum. Glacial acetic acid (9.5 mL) was added, and the solution was chilled to 0° C. A solution of TBAF (5.16 mL, 1.0M in THF) was syringed into the chilled solution, and stinting was continued at 0° C. for 8 h and then at rt for 25 hours. Methylene chloride (50 mL) was added, and the entire solution was transferred to a 250-ml separatory funnel where it was neutralized with 1M disodium phosphate solution (2×75 mL). The combined organic layers were rotary evaporated under reduced pressure and the concentrate was purified by flash chromatography (silica gel, 25–40% gradient of ethyl acetate/hexane), yielding a colorless oil (424 mg, 0.497 mmol, 95%) which later solidified upon standing; $^1$H NMR (CDCl$_3$) δ 67.36 (br. s, 20H), 5.06 (t, 1H), 4.96 (dd, 2H), 4.84 (dd, 2H), 4.75 (d, 1H), 4.59 (m, 2H), 4.53 (dd, 1H), 4.45 (dd, 1H), 4.14 (m, 2H), 3.91 (m, 2H), 3.78 (m, 6H), 2.80 (s, 1H), 1.64 (m, 2H), 1.27 (br. s, 26H), 0.90 (t, 3H).

(2S) [1-O-(2,3,4,6-Tetra-O-benzyl-β-D-glucopyranosyl)-3-O-palmitoyl] glycerol 6

Compound 4 (3.0 g, 3.1 mmol) was dissolved in THF (120mL) in a 250-mL three-necked round-bottomed flask fitted with a 60-mL addition funnel, glass stopper, and septum. TBAF (54 mL, 1.0M in THF) was added through the addition funnel over a 15 minute period. Glacial acetic acid (18 mL) measured in a graduated cylinder was then poured into the reaction mixture, and the solution was stirred for 45 minutes. The solution was concentrated under reduced pressure to approximately 30 mL of liquid and then redissolved in methylene chloride (150 mL). The organic layer was washed with water (3×120 mL) and neutralized with sodium bicarbonate solution (2×150 mL). The combined aqueous layers were extracted with methylene chloride (100 mL). The combined organic layers were dried over magnesium sulfate, filtered, and concentrated. The resulting dark red concentrate was purified by flash chromatography (silica gel, 25% ethyl acetate/hexane) to give 6 a colorless oil which corresponded to an upper TLC spot (1.3 g, 1.52 mmol) in 46% yield. $^1$H NMR (CDCl$_3$) δ 7.36 (br. s, 20H), 4.95 (m, 2H), 4.86 (m, 3H), 4.64 (d, 1H), 4.58 (m, 2H), 4.47 (d, 1H), 4.16 (m, 1H), 3.96 (dd, 1H), 3.68 (m, 8H), 2.38 (t, 2H), 1.62 (m, 2H), 1.27 (br. s, 24H), 0.96 (t, 3H). Isolation of a lower TLC spot gave a white solid (400 mg, 0.469 mmol) in 15% yield which corresponded to compound 5; $^1$H NMR (CDCl$_3$) δ 7.36 (br- s, 20H), 5.06, (t, 1H), 4.96 (dd, 2H), 4.84 (dd, 2H), 4.75 (d, 1H), 4.59 (m, 2H), 4.53 (dd, 1H), 4.45 (dd, 1H), 4.14 (m, 2H), 3.91 (m, 2H), 3.78 (m, 6H), 2.80(s, 1H), 1.64 (m, 2H), 1.27 (br. s, 26H), 0.90 (t, 3H).

Resilation of (2R) [1-O-(2,3,4,6-Tetra-O-benzyl-β-D glucopyranosyl)-2-O-palmitoyl] glycerol 5

In a nitrogen-purged 50-mL round-bottomed flask fitted with a septum was placed compound 5 (318 mg, 0.373 mmol) dissolved in DMF (8 mL). tert-Butyl-dimethylsilyl chloride (281 mg, 1.86 mmol) and imidazole (254 mg, 3.73 mmol) were added, and the solution was stirred for 22 h. Methylene chloride (50 mL) was added, and the reaction mixture was transferred to a 250-mL separatory funnel. The organic layer was washed with water (50 ml), and then the aqueous layer was extracted with methylene chloride (2×50 mL). The pooled methylene chloride layers were washed with water (2×75 mL), dried over magnesium sulfate, and the filtered. The filtrate was concentrated and purified by flash chromatography (silica gel, 14% ethyl acetate/hexane) to give 4 as a yellow oil (239 mg, 0.247 mmol) in 66% yield.

Resilation of (2S) [1-O-(2,3,4,6-Tetra-O-benzyl-β-D-glucopyranosyl)-3-O-palmitoyl] glycerol 6

In a nitrogen-purged 25-mL round-bottomed flask fitted with a septum was placed compound 6 (176 mg, 0.206 mmol) dissolved in anhyd DMF (5 mL). tert-Butyl-dimethylsilyl chloride (155 mg, 1.03 mmol) and imidazole (140 mg, 2.06 mmol) were added, and the solution was stirred for 43 h. Methylene chloride (50 mL) was added, and the reaction mixture was transferred to a 250-mL separatory funnel. The organic layer was washed with water (50 mL). The aqueous layer was extracted with methylene chloride (2 ×50 ml). The methylene chloride layers were pooled methylene and washed with water (2×75 mL), dried over magnesium sulfate, and then filtered. The filtrate was concentrated and flash chromatographed (silica gel, 14% ethyl acetate/hexane) to give 7 as a light yellow oil (190 mg, 0.223 mmol) in 95% yield; $^1$H NMR (CDCl$_3$) δ7.38 (br. s, 20H), 4.99 (dd, 2H), 4.85 (t, 2H), 4.78 (d, 1H), 4.68 (d, 1H), 4.61 (dd, 2H), 4.48 (d, 1H), 4.37 (d, 1H), 4.13 (s, 2H), 3.98 (m, 1H), 3.77 (m, 2H), 3.67 (m, 3H), 3.52 (m, 2H) 2.35 (t, 2H), 1.67 (m, 2H), 1.31 (br. s, 24H), 0.93 (s, 12H), 0.14 (s, 6H).

(2S) [1-O-(2,3,4,6-Tetra-O-benzyl-β-D-glucopyranosyl)-2-O-palmitoyl 3-O-(2-bromoethyl)benzylphosphoryl] glycerol 15

Procedure A In a nitrogen-purged 100-mL three-necked round-bottomed flask fitted with two stoppers and a septum was dissolved freshly distilled 2-bromoethylphosophorodichloridate (1.72 g, 7.11 mmol) in diethyl ether (20 mL). The solution was chilled to 0° C., and triethylamine (8.15 mL, 58.5 mmol) was injected into the solution which caused precipitation of a white solid. A solution of compound 5 (1.0 g, 1.17 mmol) in anhyd diethyl ether (55 ml) was injected into the chilled reaction mixture, and the ice bath was removed. The reaction was stirred for 30 minutes after which benzyl alcohol (1.21 mL, 11.7 mmol) was injected into the reaction mixture. Stirring was continued at rt for 5 d. The reaction was then filtered through a fritted glass funnel, and the filtrate was concentrated. The orange concentrate was purified by flash chromatography (0–33% ethyl acetate/hexane) to give 15 as a light yellow oil (566 mg, 0.501 mmol) in 43% yield; $^1$H NMR (CDCl$_3$) 67.38–7.25 (br. s, 23H), 7.16 (m, 2H), 5.26 (m, 1H), 5.10 (t, 2H), 4.94 (m, 2H), 4.81 (t, 3H), 4.71 (d, 1H), 4.61 (d, 1H), 4.55 (d, 2H), 4.39 (d, 1H), 4.25 (m, 4H), 4.08 (dd, 1H), 3.73 (m, 3H), 3.64 (dd, 2H), 3.42 (m, 4H), 2.27 (t, 2H), 1.58 (m, 2H), 1.25 (br. d, 24H), 0.89 (t, 3H).; $^{13}$C NMR (CDCl$_3$) δ173.210, 138.559, 138.362, 138.096, 138.074, 128.667, 128.622, 128.333, 128.318, 128.296, 127.962, 127.878, 127.757, 127.734, 127.696, 127.605, 127.522, 103.862, 84.540, 81.969, 71.652, 75.589, 74.937, 74.906, 74.686, 73.480, 70.469, 70.385, 69.680, 69.619, 68.777, 67.283, 66.099, 66.069, 34.170, 31.887, 29.657, 29.619, 29.596, 29.452, 29.315, 29.239, 29.080, 24,802, 22.647, 14.050.

Procedure B In a nitrogen-purged 100-mL three-necked roundbottomed flask fitted with a thermometer, stopper, and septum was dissolved freshly distilled 2-bromoethylphosphorodichloridate (1.42 g, 5.85 mmol) in methylene chloride (15 mL). The solution was chilled to 0° C., and compound 5 (1.0 g, 1.17 mmol) and a solution of N-methylmorphiline (1.28 mL, 11.7 mmol) dissolved in methylene chloride (35 mL) was injected into the solution over a 10 minute period. The reaction mixture was stirred at 0° C. for 5.5 h at which point a new TLC spot which co-spotted with secondary alcohol 6 appeared. Stirring was continued for another 30 minutes, and benzyl alcohol (1.21 ml, 11.7 mmol) was injected into the reaction. After 6 days of stirring, the reaction mixture was transferred to a 500-mL separatory funnel, and methylene chloride (150 mL) and water (200 ml) were added. The layers were separated, and the organic layer was rotary evaporated under reduced pressure. The resulting oil was flash chromatographed (silica gel, 33% ethyl acetate/hexane) to give 15 as a yellow oil (250 mg, 19%); $^1$H NMR (CDCl$_3$) δ7.38 8–7.2 5 (br. s, 23H), 7.16 (m, 2H), 5.26 (m, 1H), 5.10 (t, 2H), 4.94 (m, 2H), 4.81 (t, 3H), 4.71 (d, 1H), 4.61 (d, 1H), 4.55 (d, 2H), 4.89 (d, 1H), 4.25 (m, 4H), 4.08 (dd, 1H), 3.73 (m, 3H), 3.64 (dd, 2H), 3.42 (m, 4H), 2.27 (t, 2H), 1.58 (m, 2H), 1.25 (br. d, 24H), 0.89 (t, 3H).; $^{13}$C NMR (CDCl$_3$) δ173.210, 138.491, 138.286, 137.990, 137.975, 128.720, 128.652, 128.387, 128.364, 128.015, 127.954, 127.878, 127.810, 127.780, 127.727, 127.681, 127.613, 103.854, 84.495, 81.923, 77.781, 77.546, 75.688, 75.020, 74.808, 74.747, 73.473, 70.438, 69.642, 68.633, 67.322, 66.759, 66.129, 34.178, 31.925, 29.702, 29.664, 29.641, 29.490, 29.422, 29.368, 29.285, 29.103, 24.802, 22.700, 14.198.

(2S) [1-O-(2,3,4,6-Tetra-O-benzyl-β-D-glucopyranosyl)-2-O-palmitoyl-3-O-phosphatidylcholine] glycerol 16

A 45 mL Parr bomb equipped with a magnetic stirring bar was charged with a solution of phosphate 15 in toluene (10 mL). Condensed anhydrous trimethylamine (12 mL) was added quickly in one portion, and then the vessel was sealed and heated in an oil bath at 55° C. for 24 h. The reaction mixture was concentrated to a viscous oil and triturated with ethyl ether, upon which a white precipitate formed. the precipitate was filtered off, washed with ether, and then the combined ethereal solutions were concentrated to a glassy solid. Purification of this residue using preparative TLC (2000µ double elution with 75%,12.5%,12.5% methylene chloride/reethanol/hexanes gave inner salt 16 as a glassy solid;

(2S) [β-D-glucopyranos-1-yl-2-O-palmitoyl-3-O-phosphatidylcholine] glycerol SP-19501

A solution of phosphatidylcholine 16 (200.4 mg, 0.197 mmol) in reagent grade methanol (25 mL) was hydrogenated at 60 psi over 10% Pd/C (40 mg, 20 wt %). After 30 h, the catalyst was filtered off through celite and the methanol washing were combined and concentrated. The residue was dissolved in fresh methanol (25 mL) and resubjected to hydrogenation at 60 psi over 80 mg (40 wt %) of 10% Pd/C. After 48 h, the reaction was still incomplete. After filtration, washing of the catalyst, and concentration, the residue was subjected to hydrogenation using 400 mg (200 wt %) of Pd/C at 60 psi in methanol (25 mL). After 22 h, the catalyst was filtered off through celite and the methanol filtrate and washings were combined and concentrated to afford 92.8 mg (71.6%) of (S) SP-19501 as a white solid; $^1$H NMR (CD$_3$OD) δ5.12 (br t, 0.5 H), 4.88 (br m, 4.5 H), 4.25 (br m, 2H), 4.12–3.57(M, 12H), 3.4–3.1 (m containing singlet at 3.18, 12H), 2.3 (m, 2H), 1.55(m, 2H), 1.24 (m, 22H), 0.86 (br t, 3H); $^{13}$C NMR (CD$_3$OD) δ 74.93, 104.80, 78.02, 77.93, 75.19, doublet at 71.53 and 71.49, doublet at 70.80 and 70.73, doublet at 67.79 and 67.74, multiplet at 67.50, 62.53, doublet at 60.56 and 60.52, triplet at 54.79, 34.88, 33.15, 30.85, 30.85, 30.66, 30.56, 30.46, 30.26, 26.10 and 26.03, 23.82, 14.56; $^{31}$P NMR (CD$_3$OD) δ1.65.

(2S) 2,3-O-Isopropyiidene-1-O-trifluromethylsulfonyl-glycerol was prepared according to the method described for the corresponding (R) isomer in 92% yield and used immediately.

(2S) [1-O-(2,3,4,6-Tetra-O-benzyl-β-D-glucopyranosyl)-2,3-O-isopropylidene] glycerol 8

2,3,4,6-Tetra-O-benzyl-D-glucopyranose (65 g, 0.12 mol) was dissolved in THF (800 mL) and chilled to −10° C. in a nitrogen-purged 3-L three-necked morton flask fitted with a thermometer, stopper, and mechanical stirrer. Sodium hydride 60% in oil (33 g, 0.825 mol) was added in 4 increments over 10 minutes, and the solution was stirred for 1 h. (S) 2,3-O-Isopropylidene-1-O-trifluoromethylsulfonylglycerol (0.15 mol) dissolved in THF (200 mL) was then dropped via an addition funnel into the reaction mixture over a 20 minute period at −10° to −15° C. The solution was stirred at −10° to −15° C. for 6 hours. The reaction mixture was filtered through a short plug of silica gel and concentrated to an orange brown oil, 114 g. Purification of the crude by flash chromatography using 50% ethyl ether/hexanes gave 39.8 g (67.6%) of βepimer 8 as a white solid, along with 4 g (5.1%) of a mixture of α and β epimers; mp of β anomer 85.7°–87.2° C.; $^1$H NMR of β epimer (CDCl$_3$) δ 7.4–7.2 (m, 18H), 7.19–7.14 (m, 2H), 4.98–4.92 [overlapping doublets at 4.97 (J=10.8) and 4.94 (J=10.8), 2H], 4.82 (t, 2H, J=10.8), 4.73 (d, 1H, J=10.4), 4.63 (d, 1H, J=12.4), 4.58–4.51 [overlapping doublets at 4.55 (J=12) and 4.53 (J=10.8), 2H] 4.45 (dy 1H, J=7.2), 4.36 (p, 1H, H2), 4.08 (pseudo triplet, 1H), 3.94–3.89 [overlapping doublets at 3.92 (J=10) and 3.91 (J=9.6), 1H], 3.82–3.57 (m, 6H), 3.47 (pseudo triplet, 2H), 1.44 (s, 3H), 1.38 (s, 3H); $^{13}$C NMR (CDCl$_3$) δ 138.569 (0), 138.384 (0), 138.006 (0), 138.021 (0), 128.341, 128.258, 127.962, 127.856, 127.765, 127.696, 127.620, 127.605, 109.467 (0), 103.869 (Cl'), 84.586 (C3'), 82.075 (C2'), 77.705 (C4'), 75.680 (2), 75.005 (2), 74.815 (2 carbons, C2, C5'), 74.512 (1), 73.457 (C1), 71.151 (2), 68.785 (C6'), 67.017 (C3), 26.895 (3), 25.393 (3).

(2S) 1-O-(2,3,4,6-Tetra-O-benzyl-β-D-glucopyranosyl)—glycerol 9

A suspension of 8 (20 g, 30.5 mmol) in 60% acetic acid (800) was heated to reflux for 1 h. Workup was similar to that described for the (R) diol 2, providing 18 g (96% yield) of 9 as a white solid, which was of sufficient purity after trituration with ether for the subsequent step. Diol 9 could be recrystallized from ether/hexane, mp 89.6–90.90C; $^1$H NMR (CDCl$_3$) δ7.38–7.27 (m, 18H), 7.16 (t, J=3.5, 2H), 4.98–4.74 (m, 5H), 4.61–4.5 (m, 3H), 4.42 (d, 1H, J=8.0, H$_1$'), 3.89–3.80 (m, 3H, H$_1$'s, H2), 3.72–3.63 (m, 4H, H$_3$ H$_3$', H$_{6b}$'), 3.62–3.44 (m, 4H, H$_{6a}$', H$_4$', H$_5$', H$_2$'), 2.59 (s, 2H, OH's); $^{13}$C NMR (CDCl$_3$) δ138.370 (0), 138.119 (0),137.78 (0), 137.69 (0), 128.462, 128.447, 128.432, 128.060, 128.038, 127.962, 127.894, 127.848, 127.810. 127.704, 104.195 (C$_1$'), 84.616 (C$_3$'), 82.037 (C$_2$'), 77.736 (C$_4$'), 75.733 (2), 75.043 (2, 2 carbons), 74.466 (C$_5$'), 73.480 (2), 72.312 (C$_1$), 70.772 (C$_2$), 68.731, (C$_6$'), 63.355 (C$_3$).

(2R) [1-O-(2,3,4,6-Tetra-O-benzyl-β-D-glucopyranosyl)-3-O-tert-butyldimethylsilyl] glycerol 10

In a nitrogen-purged 100-mL round-bottomed flask fitted with a septum was dissolved diol 9 (28.0 g, 45 mmol), imidazole (5.71 g, 90 mmol), and t-butyl dimethylsilylchloride (6.92 g, 45.3 mmol) in anhyd DMF (75 mL). The reaction mixture was stirred under nitrogen overnight, transferred to a 1-L separatory funnel, and chloroform (300 mL) and water (300 mL) were added. The aqueous layer was extracted with chloroform (2×100 mL) and then the combined organic layers were washed with water (3×100 mL). After drying (Na$_2$SO$_4$) and concentration, purification by flash chromatography (silica gel, 50% ethyl ether/hexanes) gave 10 as a colorless oil (29.5 g) in 90% yield;

(2R) [1-O-(2,3,4,6-Tetra-O-benzyl-β-D-glucopyranosyl)-2-Opalmitoyl-3-O-t-butyldimethylsilyl] glycerol 11

A mixture of 10 (22.2 g, 3 0.4 mmol), palmitic anhydride (16.5 g, 33.4 mmol), dimethylaminopyridine (741 mg, 6.08 mmol), triethylamine (3.78 g, 5.2 mL, 37.3 mmol) and anhyd THF (250 mL) was stirred under nitrogen at rt overnight. The mixture was poured into a 2-L separatory funnel, diluted with diethyl ether (500 mL) and water (500 mL), and the layers separated. The aqueous layer was filtered through Whatman No. 1 paper and extracted with more diethyl ether (2×500 mL). The combined ether layer was washed with water (3×200 mL) and then dried (MgSO$_4$). Following filtration, purification by flash chromatography (silica gel, 33% ethyl ether/hexane) gave 11 as a light yellow oil, 28.2 g, 96% yield); Compound 11 could be carried on to the next transformation without chromatographic purification.

(2S) [1-O-(2,3,4,6-Tetra-O-benzyl-β-D-glucopyranosyl)-2-Opalmitoyl] glycerol 12

Crude 11 (30.4 mmol based on 10) was dissolved in THF (100 mL) and the solution was chilled to 0° C. A premixed solution of TBAF (520 mL, 1.0M in THF) which was buffered to pH=6.37 with acetic acid was added dropwise via an addition funnel at 0° C. for 1 h, and then at −15° C. overnight. The reaction mixture was concentrated, water (100 mL) was added, and the resulting mixture was extracted with chloroform (3×300 mL). The combined chloroform layer was washed with water (4×500 ML), and then the combined aqueous layer was backextracted with diethyl ether (500 mL). After drying the combined organic layer over Na$_2$SO$_4$, concentration gave a red oil which was purified by flash chromatography (50% ethyl ether/hexane). Evaporation of the product containing fractions afforded 12 as a white solid (24.6 g, 94.6% yield for two steps);

(2R) [1-O-(2,3,4,6-Tetra-O-benzyl-β-D-glucopyranosyl)-3-Opalmitoyl] glycerol 13

Compound 11 (2.33 g, 2.41 mmol) was dissolved in THF (150 mL) in a 250-mL three-necked round-bottomed flask fitted with a 60-mL addition funnel, glass stopper, and septum. After cooling the solution to OoC, TBAF (24.1 mL, 1.0M in THF) was added through the addition funnel over a 5 minute period. Glacial acetic acid (13.8 mL 241 mmol) was then poured into the reaction mixture to quench the reaction, and the resulting solution was stirred for approximately 30 minutes. The reaction mixture was poured into a separatory funnel containing ice water (500 mL) and methylene chloride (200 mL). The layers were separated, and aqueous layer was extracted twice more with methylene chloride (100 mL portions) and then the combined organic layer was washed with brine (400 mL). Following dring (MgSO4), filtration, and then concentration, purification by flash chromatography using 1/5 EtoAc/hexanes gave secondary alcohol 13, 0.96 g (46.8%), as a colorless oil; Further elution gave 238 mg (11.6%) of primary alcohol 12; Also isolated was a mixture of the two alcohols in 5.3% yield. Resilation of (2S) [1-O-(2,3,4,6-Tetra-O-benzyl-β-D glucopyranosyl)-2-O-palmitoyl] glycerol 12

The identity of 12 was established by resilylation of 12 according to the procedure described above for the (R) isomer, compound 5.

(2R) [1-O-(2,3,4,6-Tetra-O-benzyl-β-D-glucopyranosyl)-2-O-palmitoyl-3-O-(2-bromoethyl) benzylphosphoryl] glycerol 17

In a nitrogen-purged 1-L three-necked morton flask fitted with two stoppers and a septum was dissolved freshly distilled 2-brorhoethylphosphorodichloridate (17.2 g, 71.1 mmol) in anhyd diethyl ether (500 mL). The solution was chilled to 0° C. and triethylamine (81.5 mL, 0.585 mol) was injected into the solution, causing precipitation of a white solid. A solution of 12 (10.0 g, 11.7 mmol) dissolved in diethyl ether (250 mL) was cannulated into the morton flask, and the solution was stirred for 1.5 hours. TLC showed disappearance of 12. Benzyl alcohol (12.1 mL, 0.117 mol) was injected into the reaction mixture, and stirring was continued at rt for 16 h. The reaction mixture was then filtered through a fretted glass funnel. Filtrate was then concentrated and purified by flash chromatography twice. First chromatography (silica gel, 33% ethyl acetate/hexane) and second chromatography (silica gel, 25% ethyl acetate/hexane) gave 17 as a light oil (5.5 g) in 42% yield;

(2S) [1-O-(2,3,4,6-Tetra-O-benzyl-β-D-glucopyranosyl)-Opalmitoyl-3-O-phosphatidylcholinel glycerol 18

A 45 mL Parr bomb was equipped with a magnetic stir bar and then charged with a solution of 17 (1.17 g, 1.04 mmol) in benzene (15 mL). Anhyd trimethylamine (15 mL, 0.145 mmol) which had been condensed at −78° C. was quickly poured into the reaction vessel, and the bomb was sealed. The reaction was stirred at 55° C. in an oil bath for 24 hours behind a blast shield. The bomb vessel was then cooled to −78° C., opened, and left in a hood to evaporate trimethylamine. The remaining solution was rotary evaporated under reduced pressure, and the oily concentrate was dissolved in methylene chloride and purified by preparative TLC (2000μ)- Double elution with 75%; 12.5%:12.5% methylene chloride/methanol/hexane gave inner salt 18 as an opaque glassy solid (223 mg, 21%). $^1$H-NMR (CDCl$_3$) δ0.32 (br. s, 20H), 5.21 (m, 1H), 4.90 (dd, 2H), 4.82 (m, H), 4.64 (m, 2H), 4.50 (t, 2H), 4.42 (d, 1H), 4.22 (br. s, 3H), 3.95 (s, 2H), 3.72 (s, 2H), 3.62 (t, 2H), 3.55 (s, IH), 3.40 (m, 4H), 3.10 (s, 9H), 2.19 (m, 2 H), 1.47 (m, 2H), 1.20 (br. d, 24H), 0.87 (t, 3H). $^{13}$C-NMR (CDCl$_3$) δ73.393, 138.453, 138.377, 138.051, 137.998, 128.470, 128.417, 128.356, 128.318, 128.235, 128.053, 128.007, 127.947, 127.856, 127.780, 127.719, 127.636, 127.567, 103.899, 84.472, 81.984, 77.478, 77.394, 77.311, 77.190, 75.672, 74.944, 74.550, 73.336, 68.663, 68.489, 59.158, 59.135, 54.409, 54.349, 34.246, 31.902, 29.710, 29.664, 29.535, 29.353, 29.330, 29.148, 24.7871 22.678, 14.121.

(2R) [βD-glucopyranos-1-yl-2-O-palmitoyl-3-O-phosphatidylcholine] glycerol SP-19501

A solution of phosphatidylcholine 18 (130 mg, 0.127 mmol) in reagent grade methanol (25 mL) was hydrogenated at 60 psi over 10% Pd/C (52 mg, 40 wt %)- After 23 h, TLC showed an incomplete reaction- The catalyst was filtered off through celite and the methanol washings were combined and concentrated- The residue was dissolved in fresh methanol (25 mL) and resubjected to hydrogenation at psi over 240 mg (185 wt %) of 10% Pd/C. After 20 h, the reaction was complete by TLC. The catalyst was filtered off through celite and the methanol filtrate and washings were combined and concentrated to afford 64.0 mg (76.6%) of (R) SP-19501 as a white solid; $^1$H NMR (CDCl$_3$) δ5.19 (m, 1H), 4.97 (s, OH+HDO), 4.34–4.26 (br m, 2H), 4.16–3.95 (m, 3H), 3.9–3.6 (m, 6H), 3.42–3.14 (multiplet containing singlet at 3.24, 13H), 2.37 (t, J=7.6, 2H), 1.62 (pseudo t, 2H), 1.31 (m, 24H), 0.92 (t, J=7.2, 3H); $^{13}$C NMR (CD$_3$OD) δ175.02, 104.88, 78.07, 78.04, 75.04, 72.97, 72.89, 71.52, 68.56, multiplet at 67.50, doublet at 64.99 and 64.94, 62.65, doublet at 60.52 and 60.48, triplet at 54.74 (J=3.1), 35.14, 33.13, 30.85, 30.69, 30.54, 30.29, 26.01, 23.79, 14.50; 31P NMR (CD$_3$OD) δ1.35

(2R)1-[Benzyl-(2'bromoethyl)-phosphproyl]-2,3-isopropylidene glycerol (19)

2-Bromoethylphosphodichloridate (20.0 g, 0.08 mol) was dissolved in CCl4 (50 ml) in a nitrogen-purged 0.5 L three-necked flask fitted with a magnetic stir bar, thermometer, and a 125-ml addition funnel. The solution was chilled to 0° C., and to this stirred solution was added dropwise the solution of (S)-form solketal (10.7 g, 98 mol %) and N-methyl-morpholine (8.22 g,98 mol %) in CCL4 (25 ml). After 2 hours TLC showed disappearance of solketal. To the reaction mixture was added dropwise the solution of benzyl alcohol (44.6 g, 500 mol %) and N-methylmorpholine (8.38 g, 100 mol %). The reaction mixture was stirred under nitrogen for 60 hours at room temperature. TLC showed the complete reaction. The reaction mixture was filtered through Short filter #C, and the solution was rotary evaporated to volume near 70 ml and purified by flash chromatography (silica gel, diethyl ether) to give colorless oil (15.1 g, 0.04 mol) in 45% yield; $^1$HNMR (CDCL3) δppm: 7.40 (br. s 5 H), 5.2 (d, 2 H), 4.3 (br.s, 3 H), 4.0 (br.s, 3 H), 3.85 (br.s,1 H), 3.2 (s, 2 H), 1.4 (d, 6H); $^{13}$C NMR (CDCL3): 128.743, 128.682, 128.645, 128.114, 128.076, 109.885, 77.364, 77.046, 76.727, 73.920, 73.837, 69.771, 69.710, 67.760, 67.707, 67.654, 66.774, 66.721, 65.955, 29.353, 29.277, 26.683, 25.204; $^{31}$P NMR (2R)1-[Benzyl-(2'-bromoethyl)-phosphoroyl] 1-2,3-dihydroxy glycerol (20)

A nitrogen purged 1L roundbottomed flask fitted with septum was charged with compound 19 (19.5 g, 0.048 mol) in dry THF (50 ml) and the solution of 1M H3PO4 (800 ml) was added. The reaction mixture was stirred under nitrogen by room temperature for 15 hours. TLC showed the completness of the reaction. Then the reaction mixture was transferred to a 2 L sepapatory funnel. The acidic layer was extracted with ethyl acetate (7×450 ml). The combined organic extract was washed with water (2×850 ml). After drying over sodium sulfate it was rotary evaporated and dryed in high vacuo for 10 hours to give a colorless oil (14 g, 0.04 mol %) in 80% yield; $^1$H NMR (CDCl3), δppm: 7.38 (br.s, 5H), 5.2 (d, 2H), 4.25–3.8 (multiplet, 6 H), 3.7–3.25 (br.m 5 H) $^{13}$C NMR (CDCl3): 77.789, 77.774, 77.349, 77.030, 76.712, 70.522, 70.491, 70.461, 70.431, 70.097, 70.044, 68.898, 68.883, 68.822, 67.085, 67.032, 62.617, 62.496, 42.363, 42.280; $^{31}$P NMR (CDCl3): −0.485 (85% H3PO4).

(2R)1-[Benzyl-(2'-bromoethyl)-phosphoroyl-2-hydroxy-3-O-triphenylmethyl glycerol (21)

To a stirred solution of diol 20 (8.0 g, 21.6 mmol) in DMF (16 nil) was added diisopropylethylamine (4 ml, 105 mol %) followed by addition of trityl chloride ( 6.4 g, 105 mol %). After 40 hours at room temperature under nitrogen the reaction was complete by TLC. The reaction mixture was diluted twice with water and extracted with diethyl ether (4×100 ml). The combined extract was dryed over sodium sulfate, concentrated and purified by flash chromatography silica gel, ethyl acetate:hexane,1:1) to give 21 as a light oil 6.9 g (52.1%); $^1$H NMR (CDCl3) δ0.2–7.5 (br.m, 20 h), 5.07 (t, 2H), 4.12–4.26 (m,4H), 3.44 (dd 2H), 2.05 (s, 1H), 1.26 (t, 1H). $^{13}$C NMR (CDCl3): 138.772, 124.017, 123.911, 123.820, 123.342, 123.266, 123–152, 122.462, 122.417, 72.593, 72.274, 71.955, 65.105, 65.090, 65.030, 65.014, 64.954, 64.893, 62.109, 62.056, 58.877, 24.680, 24.604. $^{31}$P NMR (CDCl3) −0.158 (s).

(2R) 1-[Benzyl-(2'-bromoethyl)-phosphoroyl-2-O-palmitoyl-3-O-triphenyl methyl glycerol (22)

To a stirred solution of compound 21 (6.9 g, 11.3 mmol) in dry THF (90 ml) was added triethylamine (1.79 ml, 1 10,mol %), palmitic anhydride (6.13 g, 1 10 mol %) and dimethylaminopyridine (276 mg, 20 mol %). The reaction was stirred under nitrogen for 3 hours untill TLC showed disappearance of the starting material 21. The reaction mixture was rotary evaporated to a small volume and purified by flash chromatography (silica gel, diethyl ether:hexane, 1:3 to elute UV-nonactive impurities, diethyl ether:hexane,1:1to elute compound 22). Yield 8.8 g (92.6%0, colorless oil, $^1$HNMR (CDCl3) 7.41–7.22 (m, 20 H), 5.20 (d, 1H), 5.04 (t, 2H), 4.23 (m, 4H), 3.58 (s, 1H), 3.41 (s, 1H), 3.23 (s, 2H), 2.33 (t, 2H), 1.62 (m, 3H), 1.24 (s, 24H), 0.88 (t, 3H). $^{13}$C NMR 172.984, 143.407, 143.285, 128.675, 128.607, 128.576, 128.523, 127.985, 127.848, 127.180, 127.135, 86.672, 77.319, 77.000, 76.681, 70.901, 70.818, 69.604, 69.581, 66.463, 66.440, 61.828, 34.284, 31.894, 29.672, 29.634, 29.611, 29.437, 29.346, 29.285, 29.247, 29.232, 29.141, 29.095, 24.832, 22.678, 14.121. $^{32}$P NMR (CDCl3)−1.327.

(2R)1-[Benzyl(2'-bromoethyl)-phosphoro]-yl-2-O-palmtoyl-3-hydroxy glycerol 23

Procedure A

To a stirred solution of compound 22 (3.2 g, 3.76 mmol) in 45 ml THF was added 45 ml 96% formic acid. After 2 hours qt room temperature the reaction was coplete by TLC. The reaction mixture was diluted twice with water, neutralized with sodium bicarbonate (3×300 ml). The combined extract was washed with water, dryed over sodium sulfate, rotary evaporated to a small volume and purified by flash chromatography (silica gel, ethyl acetat: hexane, 1:3 to. elute less polar impurities, ethyl acetat:hexane,1:1to elute compound 23. Yield 1.65 g (72.7%), colorless oil.

Procedure B

A nitrogen purged 0.5 L round-bottomed flask fitted with condenser was charged with compound 22 (1 g, 1.17 mmol) in dry benzene (230 ml) in the presence of anhydrous CuSO4 (17.6 g). The reaction mixture was stirred at room temperature for 15 hours and then reflux for 2 hours untill the reaction was complete by TLC. The CuSO4 was filtered off through Shott filter #C and concentrated in vacuo and purified by flash chromatography (silica gel, ethyl acetate/ hexane, 1:1) to give a light yellow oil (0.47 g, 0.77 mmol) in 66% yield. $^1$HNMR (CDCl$_3$): α7.40 (br. s, 5H), 5.2 (d, 2H), 4.2 (mult, 8H), 2.32 (t, 1H), 1.62 (pseudo t, 2H), 1.31 (m, 24H), 0.88 (t, 3H). $^{13}$C NMR (CDCl3): 130.898, 123.872, 128.789, 128.698, 128.538, 128.516, 128.114, 127.886, 126.968, 77.326, 77.008, 76.689, 70.097, 70.074, 69.012, 68.951, 68.633, 68.604, 68.572, 68.542, 67.085, 67.047, 67.032, 66.994, 65.272, 64.195, 62.731, 62.716, 34.041, 31.902, 29.672, 29.588, 29.505, 29.444, 29.338, 29.239, 29.103, 24.749, 22.670, 14.113. 31 P NMR: −3.069 (85% H3PO4).

(2R)-1-O-(2,3.4.6-Tetra-O-benzyl-β-D-gluco-pyranosyl)-2'-O-palmitoyl-3'-O-[benzyl(2"-bromoethyl)- phosphoril]-glycerol (17)

To a stirred solution of O-(α-D-glucopyranosyl) trichloroacetimidate (24)(390 mg, 115 mol %) in dry methylene chloride (3 ml) was added dropwise a solution of compound 6 (300 mg, 0.49 mmol) and boron trifluoride etherate (70 mg, 100 mol in dry methylene chloride (3 ml). The reaction mixture was stirred under nitrogen for 2 hours at room temperature, then more compound 24 (100 mg, 35 mol %) was added to bring the reaction to the end. After 4 h, the reaction mixture was evaporated to a small volume and separated by flash chromatography (silica gel, diethyl ether/hexane, 1:3) to give compound 17 as a colorless oil (120 mg, 22%), which was identical to the material described earlier.

6.4. Antifungal Activity

The antifungal activity of the isolated phosphocholine fraction was determined in vitro by using three fungal cultures—*Candida albicans, Cryptococcus neoformans* and *Aspergillus fumigatus*. The method used to determine in vitro antifungal activity is discussed in McGinnis, M. R., *Laboratory Handbook of Medical Mycology*, Academic Press, New York, London, p661 (1980); and Droughet E., Dupont, B., Improvisi, L., Vivian, M. A. and Tortorano, A. M., "Disc agar diffusion and microplate automatized technics for in vitro evaluation of antifungal agents on yeast and sporulated pathogenic fungi" in *In Vitro and In Vivo Evaluation of Antifungal Agents*, Eds. Iwata, K. and Vanden Bossche, H., Elsevier Science Publishers, New York, Oxford p303 (1986).

Avanti Biolipids have also been found to have high antifungal activities. A summary of the antifungal screening test is shown in table 2. The analog compounds were tested for their activity against C. albicans, C. neoformans, A. fumigatus and T. rubrum. Partial inhibition of the fungus of between 25 to 75% was measured along with the total inhibition (MIC) by these anolog compounds. A description of the partial inhibition measurement can be found in R. L. Stiller, et al *The Journal of Infectious Diseases*, 147, No. 6 (1983). The structure of these analog compounds is as follows.

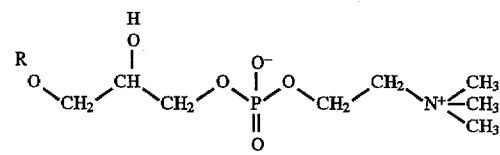

wherein R is the group identified in table 2.

TABLE 2

| | Test Results from Antifungal Screening Laboratory | | | | | | | |
|---|---|---|---|---|---|---|---|---|
| | MIC (µg/ml) | | | | Partial inhibition (µg/ml) | | | |
| Lecithin | CA | CN | AF | TR | CA | CN | AF | TR |
| L-a-Lysophosphatidylcholine Heptadecanoyl (C17:0) | 63 | 16 | >1000 | 63 | 16 | n/a | 31 | 31 |
| L-a-Lysophosphatidylethanol Amine, Oleoyl (C18:1,[cis]-9) | >100 | >100 | >100 | >100 | >100 | 100 | >100 | >100 |
| L-a-Lysophosphatidylcholine Decanoyl (C:10) | >500 | 500 | >500 | >500 | 250 | 250 | >500 | >500 |
| L-a-Lysophosphatidylcholine Lauroyl (C12:0) | 500 | 125 | 125 | 250 | n/a | 31 | n/a | 63 |
| L-a-Lysophosphatidylcholine Myristoyl (C14:0) | 31 | 31 | 125 | 31 | n/a | n/a | 31 | n/a |
| L-a-Lysophosphatidylcholine Stearoyl (C18:0) | >250 | >250 | >250 | >250 | >250 | 31 | >250 | >250 |
| L-a-Lysophosphatidylcholine Oleoyl (C18:1,[Cis]-9) | 31 | 31 | 63 | 31 | n/a | n/a | 31 | n/a |
| L-a-Lysophosphatidylcholine Palmitoyl (C16:0) | 31 | 31 | 63 | 500 | n/a | n/a | 31 | 63 |
| L-a-Lysophosphatidyl inositol | >100 | >100 | 100 | >100 | >100 | 100 | n/a | >100 |

The minimum inhibitory concentration (MIC) and the minimum fungicidal concentration (MFC) are summarized in the table 1 below.

| Fungus Culture | MIC (ug/ml) | MFC (ug/ml) |
|---|---|---|
| C. albicans | 0.8 | |
| C. neoformans | <0.1 | |
| A. fumigatus | <0.1 | <0.4–0.8 |

These results clearly indicate the significant antifungal activity of the isolated fraction containing against a variety of fungal cultures.

6.5. Antifungal Activities of the Phosphocholine Derivatives Class

A series of related analogs to 2-palmitoyl-1-O-glucopyranosyllysolecithin obtained commercially from 6.6. Toxicity The toxicity of the isolated phosphocholine derivative fraction is low, based on tests with Hep 2 cells indicating an $ID_{50}$ of greater than 1000 ug/ml. The method used in determining cytotoxicity is discussed in Mosmann, T.,"Rapid colorimetric assay for cellular growth and survival: application to proliferation and cytotoxicity assays", *J. Immun. Methods*, 65, 55–63, 1986.

The isolated fraction having the above-described in vitro antifungal activity and low toxicity is expected to similarly exhibit significant in vivo antifungal activity against fungal infections which are dermatophytic, systemic, ophthalmic and vaginal. Other human and animal infections treatable with the compounds of the present invention include aspergilliosis, candidiasis, and cryptococcus infections.

It is expected that the same isolated fraction would be useful in treating fungal infestation in plants as well.

It is apparent that many modifications and variations of this invention may be made without departing from the spirit and scope thereof. The specific embodiments described are given by way of example only and the invention is limited only by the terms of the appended claims.

A number of references are cited in the present specification, the entire disclosure of each of which is incorporated by reference herein, in its entirety.

What is claimed is:

1. A composition comprising a bis-phosphocholine derivative obtained from *Irlbachia alata* characterized by:

(a) IR spectrum having peaks at approximately 1060, 1220, 1475, 1600–1700, 2850, 2950, and 3400 cm$^{-1}$;

(b) $^1$H NMR spectrum having major peaks at δ1.2, 1.4, 1.7, 3.1, 3.5, 3.7 and 4.3; and (c) FAB/MB mass spectrum having major peaks (>40%) at m/z 657, 612, 587, 586, 555, 493, 491, 475, 403, 277, 233, 201, 194, 179, 168, 165 and 163.

2. The composition according to claim 1 wherein the bis-phosphocholine derivative is characterized by an HRMS (FAB$^+$) spectrum having a molecular ion at 673.4669 amu.

3. A composition comprising a bis-phosphocholine derivative obtained from *Irlbachia alata* by a method which comprises:

(a) extracting the whole plant, the leaves, the stems, the roots or the latex of the plant *Irlbachia alata* with a lower alcohol of about 1–3 carbons, acetone, water or other water miscible solvent or combinations thereof to obtain an aqueous soluble fraction;

(b) subjecting the aqueous fraction to butanol extraction and the butanol soluble fraction to gel filtration using water or water and a water miscible solvent with or without a buffer as the mobile phase; or to reversed phase column chromatography using water or water and a water miscible solvent as the mobile-phase; or to gel permeation chromatography using water or water and water miscible solvent and acetonitrile with or without a buffer as the mobile phase; or combination thereof and (c) collecting the fractions detected by NMR spectroscopy.

4. A pharmaceutical composition which is useful in treating a fungal infection when administered to a warm-blooded animal comprising a therapeutically effective amount of an antifungal agent comprising a compound having the structure of:

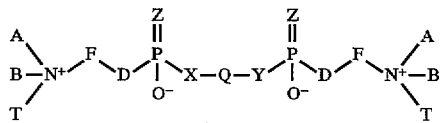

where Q is C2 to C30 alkyl, alkenyl, alkynyl, branched alkyl, branched alkenyl, or branched alkynyl;

Z is oxygen or sulfur; X and Y are independently oxygen, sulfur, CH$_2$ or N-R$_1$;

A, B, and T are independently alkyl, alkenyl, alkynyl, branched alkyl, branched alkenyl, or branched alkynyl radicals of C1 to C20 chain lengths; or are independently or together cycloalkyl or bridged cycloalkyl radicals of ring size C3 to C20, or cycloalkenyl radicals of ring size C4 to C20;

D is oxygen, sulfur, CH$_2$ or N-R$_2$;

F is alkyl, alkenyl, alkynyl, branched alkyl, branched alkenyl, branched alkynyl, cycloalkyl, bridged cycloalkyl, cycloalkenyl or cycloalkynyl radicals containing C1 to C20 carbon atoms;

R$_1$ and R$_2$ are independently hydrogen, alkyl, alkenyl, alkynyl, branched alkyl, branched alkenyl, branched alkynyl, cycloalkyl, bridged cycloalkyl, or cycloalkenyl radicals containing C1 to C20 carbon atoms, or a protecting group; and a pharmaceutically acceptable carrier.

5. A compound having the structure of:

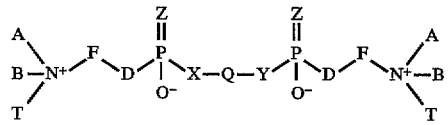

where Q is C2 to C30 alkyl, alkenyl, alkynyl, branched alkyl, branched alkenyl, or branched alkynyl;

Z is oxygen or sulfur; X and Y are independently oxygen, sulfur, CH$_2$ or N-R$_1$;

A, B, and T are independently alkyl, alkenyl, alkynyl, branched alkyl, branched alkenyl, or branched alkynyl radicals of C1 to C20 chain lengths; or are independently or together cycloalkyl or bridged cycloalkyl radicals of ring size C3 to C20, or cylcoalkenyl radicals of ring size C4 to C20;

D is oxygen, sulfur, CH$_2$ or N-R$_2$;

F is alkyl, alkenyl, alkynyl, branched alkyl, branched alkenyl, branched alkynyl, cycloalkyl, bridged cycloalkyl, cycloalkenyl or cycloalkynyl radicals containing C1 to C20 carbon atoms;

R$_1$ and R$_2$ are independently hydrogen, alkyl, alkenyl, alkynyl, branched alkyl, branched alkenyl, branched alkynyl, cycloalkyl, bridged cycloalkyl, or cycloalkenyl radicals containing C1 to C20 carbon atoms, or a protecting group.

6. The compound having the structure of:

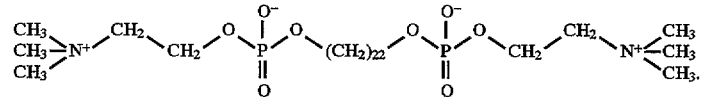

7. A method for treating a fungal infection in a warm-blooded animal comprising administering to the warm-blooded animal a therapeutically effective amount of the composition of claim 4.

8. The method of claim 7, wherein the composition is administered intravenously, intraperitoneally, subcutaneously, intramuscularly, orally, topically, by aerosol of combinations thereof.

9. The method of claim 8, wherein the compound is administered intravenously in a range of about 0.1 to about 10 mg/kg.

10. The method of claim 8, wherein the compound is administered intraperitoneally in a range of about 0.1 to about 10 mg/kg.

11. The method of claim 8, wherein the compound is administered subcutaneously in a range of about 1 to about 20 mg/kg.

12. The method of claim 8, wherein the compound is administered intramuscularly in a range of about 1 to about 20 mg/kg.

13. The method of claim 8, wherein the compound is administered orally in a range of about 5.0 to about 30 mg/kg.

14. The method of claim 8, wherein the compound is administered topically in a range of about 5.0 to about 15% by weight.

15. The method of claim 8, wherein the compound is administered by aerosol in a range of about 5.0 to about 30 mg/kg/day.

16. The composition of claim 4, wherein the compound has the structure:

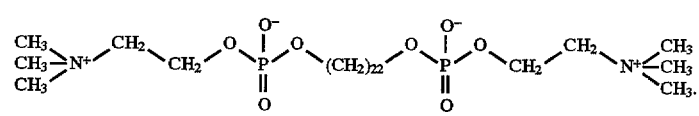

* * * * *